US009220269B2

(12) United States Patent
Mik et al.

(10) Patent No.: US 9,220,269 B2
(45) Date of Patent: Dec. 29, 2015

(54) USE OF 6-SUBSTITUTED 9-HALOGENALKYL PURINES FOR REGULATION OF GROWTH AND DEVELOPMENT OF WHOLE PLANTS, PLANT CELLS AND PLANT ORGANS; NOVEL 6-SUBSTITUTED 9-HALOGENALKYL PURINES

(75) Inventors: Vaclav Mik, Odry (CZ); Lucie Szucova, Olomouc (CZ); Karel Dolezal, Hlubocky (CZ); Lukas Spichal, Olomouc (CZ); Petr Galuszka, Olomouc (CZ); Miroslav Strnad, Olomouc (CZ); Jiri Gruz, Bohunovice (CZ)

(73) Assignee: UNIVERZITA PALACKEHO V OLOMOUCI, Olomouc (CZ)

( * ) Notice: Subject to any disclaimer, the term of this patent is extended or adjusted under 35 U.S.C. 154(b) by 79 days.

(21) Appl. No.: 13/821,163

(22) PCT Filed: Sep. 2, 2011

(86) PCT No.: PCT/CZ2011/000086
§ 371 (c)(1),
(2), (4) Date: Mar. 28, 2013

(87) PCT Pub. No.: WO2012/031574
PCT Pub. Date: Mar. 15, 2012

(65) Prior Publication Data
US 2013/0210632 A1 Aug. 15, 2013

(30) Foreign Application Priority Data
Sep. 7, 2010 (CZ) .................................... 2010-670

(51) Int. Cl.
*A01N 43/90* (2006.01)
*C07D 473/34* (2006.01)
(52) U.S. Cl.
CPC .............. *A01N 43/90* (2013.01); *C07D 473/34* (2013.01)
(58) Field of Classification Search
CPC ............................... C07D 473/34; A01N 43/90
USPC ........................... 544/277; 514/263.23, 263.4
See application file for complete search history.

(56) References Cited

U.S. PATENT DOCUMENTS 3,213,095 A 10/1965 Bambury et al.
2008/0039321 A1* 2/2008 Bastiaans et al. ............. 504/136
2009/0170879 A1* 7/2009 Szucova et al. ............ 514/263.4

FOREIGN PATENT DOCUMENTS

WO WO 03/040144 A2 5/2003

OTHER PUBLICATIONS

Mik, Vaclav. Phytochemistry 72 821-831, available online Feb. 25, 2011.*
Letham, D. S. J Plant Growth Regul (1991) 10:107-113.*
Ramzaeva. J. Org. Chem. USSR (1988), 24(5) 1090-4.*
Freudenrich, Craig. "How Cloning Works" Mar. 26, 2001. HowStuffWorks.com. <http://science.howstuffworks.com/life/genetic/cloning.htm>.*
Hilda, Zavaleta-Mancra. Journal of Plant Physiology 164 (2007) 1572-1582.*
Pernisova, Marketa. PNAS 106:9. (2009) 3609-3614.*
Letham, D.S. Plant Physiol (1989) 89, 74-77.*
Patani, George. Chem. Rev. 1996, 96, 3147-3176.*
Zhang R et al: "Cytokinin Biochemistry in Relation to Leaf Senescence III. The Senescence-retarding Activity and Metabolism of 9-substituted 6 Benzylaminopurines in Soybean Leaves" Journal of Plant Growth Regulation Springer Verlag, New York, NY, US,vol. 8. No. 3. Jan. 1, 1989, pp. 181-198.
Hashizume et al: "Synthesis and Biological Activity of Some New 6 Benzylamino 9 Alkylpurines" Plant Growth Substances 1973: Proceedings of the 8th International Conference on Plant Growth Substances Held in Tokyo, Japan. Sep. 1, 1973, Hirokawa Publ. JP, Jan. 1, 1974, pp. 462-467.
Brathe A et al: "Synthesis of 6-alkenyland 6-alkynylpurines with Cytokinin Activity" Tetrahedron, Elsevier Science Publishers, Amsterdam, NL,vol. 1, 55. No. 1. Jan. 1, 1999, pp. 211-228.
N P Ramzaeva, M Y Lidak, Y S Gol'dberg, M V Shimanskaya: "Alkylation of 6-substituted purines by .alpha.-bromo-.omega.-halogenoalkanes under conditions of phase-transfer Catalysis" J. Org. Chem. USSR (Engl. Transl.), vol. 24. 1988. pp. 984-987.
N P Ramzaeva et al: "Alkylation of Some 6-substituted Purines under Interphase Catalysis Conditions", Chemistry of Heterocyclic Compounds, Jan. 1, 1987, pp. 93-98, URL:http://www.springerlink.comjcontentjug23982050w22221/fulltext.pdf.
79 6-benzylaminopurine Plant growth regulator In: "The Pesticide Manual—A World Compendium—15th Edition", Jan. 1, 2009, British Crop Protection Council, United Kingdom.
Tony Storr: "Practical Biotechnology: Cloned Cauliflower", Plant Tissue Culture: Experimenting with Industry No. 13, Jan. 1, 1995, URL:http://www.ncbe.reading.ac.ukjncbejprotocols/PRACBIOTECH/PDFjcauli.pdf.

(Continued)

*Primary Examiner* — Golam M M Shameem
*Assistant Examiner* — Laura Daniel
(74) *Attorney, Agent, or Firm* — Notaro, Michalos & Zaccaria P.C.

(57) ABSTRACT

The invention relates to 6-substituted 9-halogenalkyl purine derivatives of the general formula I wherein R6 is selected from the group comprising —NH-furfuryl, —NH-(4-hydroxy-3-methylbut-2-en-1-yl), —NH-(3-methylbut-2-en-1-yl), —NH-(4-hydroxy-3-methylbutyl), —NH-(4-hydroxy-1,3-dimethylbut-2-en-1-yl), —NH-(4-hydroxy-1,3-dimethylbutyl), —NH-benzyl, —NH-phenyl, wherein benzyl, furfuryl and phenyl can be unsubstituted or optionally substituted with 1 to 3 substituents selected from the group comprising hydroxy, halogen, methyl and methoxy, and R9 is selected from the group comprising $C_1$-$C_3$ alkyl or $C_1$-$C_3$ alkenyl wherein each of the groups is substituted with one or more halogen atoms, for use in the regulation of growth and development of plant cells, organs and/or whole plants. The invention also relates to preparations containing these derivatives and to novel to 6-substituted 9-halogenalkyl purines.

19 Claims, 2 Drawing Sheets

(56) References Cited

OTHER PUBLICATIONS

Werner T et al: "Cytokinin-deficient transgenic Arabidopsis plants show multiple developmental alterations indicating opposite functions of cytokinins in the regulation of shoot and root meristem activity", The Plant Cell. American Society of Plant Biologists. US.bvol. 15, No. 11, Nov. 1, 2003, pp. 2532-2550.

Elliott D C et al: "Structural Analogs in the Study of Cytokinin Action", Plant Growth Substances 1970 : Proceedings of the 7. International Conference on Plant Growth Substances Held in Canberra, Australia, Dec. 11, 1970, Jan. 1, 1972, pp. 459-466.

Gan et al: "Inhibition of Leaf Senescence by Autoregulated Production of Cytokinin", Science, American Association for the Advancement of Science, Washington, DC, US, vol. 270, Dec. 22, 1995, pp. 1986-1988.

* cited by examiner

USE OF 6-SUBSTITUTED 9-HALOGENALKYL PURINES FOR REGULATION OF GROWTH AND DEVELOPMENT OF WHOLE PLANTS, PLANT CELLS AND PLANT ORGANS; NOVEL 6-SUBSTITUTED 9-HALOGENALKYL PURINES

FIELD OF ART

The invention relates to the use of 6-substituted 9-halogenalkyl purines for regulation of growth and development of plants, plant organs and cells, to preparations containing these derivatives and to novel 6-substituted 9-halogenalkyl purines.

BACKGROUND ART

Plant hormones cytokinins (CKs) play a crucial role in various physiological processes such as plant development, stress or senescence. Their levels are very precisely regulated in various tissues or subcellular compartments. The mechanism of CKs regulation is mediated by proteins participating in the CKs biosynthesis and activation, degradation, transport or perception. Cytokinin dehydrogenases (CKX, EC 1.5.99.12) are the enzymes that inactivate CKs hormones by irreversible degradation of their molecule. There are several isoforms of CKX in plants, wherein each isoform has a different specificity for the cytokinins (Bilyeu et al. 2001, Plant Phys. 125:378; Šmehilová et al. 2009, J. Exper. Bot. 60:2701). A study of transcript levels of CKX isoforms in the leaves of Arabidopsis, maize and barley revealed different expression patterns among the isoforms during leaf senescence and stress, accounting for a confirmed decrease of cytokinins. On the contrary, it was shown that the CK metabolism is accelerated during salt and osmotic stress as evidenced by a moderate increase of CK active forms (Vyroubalová et al. 2009, Plant Physiol. 151:433). Taken together, these observations suggest distinct roles of different CKs forms during various physiological processes such as abiotic stress (Kuiper et al. 1990, Plant and Soil 123, 243; Davies & Zhang 1991, Ann. Rev. Plant Physiol. Plant Mol. Biol. 42, 55; Havlová 2008, Plant Cell Env. 31:341) or senescence (Eisinger 1977, Plant Phys. 90, 1316; Lara et al. 2004, Plant Cell 16:1276). However, the exact role of the cytokinins in the mentioned processes, especially during leaf senescence, has yet to be elucidated. Leaf senescence is a key step in the life cycle of annual plants, playing an indispensable role in plant reproduction, productivity, or plant survival by means of stress handling. The senescence is the last step of leaf development occurring in an age-dependent manner, which was shown to be a complex and highly regulated process. During this process, in a senescing leaf, the stored nutrients are re-mobilized and the following degradative processes take place leading to sustaining of younger, fully developing organs such as young leaves, fruits or grains. One of the conspicuous visual symptoms of leaf senescence is the loss of chlorophyll pigments (yellowing), which is caused by replacing the chloroplast content by the products of cell degradation processes. The leaf yellowing is further followed by desiccation and eventual abscission. On the cellular or molecular level, the processes contributing to these visual symptoms include, in addition to chloroplast disintegration, also loss of proteins and nucleic acids of the cell. Molecular fundamentals of these events are under the control of very varied plant regulatory mechanisms. Although the senescence occurs in an age-dependent manner in many species, its initiation and progression can be modulated by a variety of environmental factors such as temperature, mineral deficiency, and drought conditions, as well as by internal factors such as plant growth regulators. The leaf senescence is generally balanced by a range of phytohormones, wherein the cytokinins decrease is correlated with senescing processes in the leaves (Winkler et al. 2006, J. Exper. Bot. 57:391). Moreover, it was shown that exogenous application of cytokinins inhibits the degradation of chlorophyll and proteins of the photosynthetic apparatus (He et al 2005, J. Exper. Bot. 56, 1117-1128). The strategy leading to delayed senescence involved the transgenic expression of isopentenyltransferase (IPT; 2.5.1.27), an enzyme of the cytokinin biosynthetic pathway. The transgenic plants with elevated cytokinin levels showed delayed senescence (Gan et al. 1995, Science 270:1986). A different approach to maintaining sufficient levels of active cytokinins within plant tissues employs the inhibition of cytokinin dehydrogenase. However, the cytokinin-deficient transgenic plants did not show any earlier onset of leaf senescence (Werner et al. 2003, Plant Biol. 8:371). Consequently, it is not proven yet whether the decrease in the cytokinin levels acts as a trigger of senescence or whether it is only a senescence accompanying phenomenon. Furthermore, numerous enzymes implicated in providing essential activities for the initiation and progression of the senescence include proteases, nucleases, and other degradative enzymes, as well as enzymes involved in chloroplast dismantling and chlorophyll breakdown, which were indicated to be co-induced by cytokinins. The nutrients remobilization and the sustenance of other plant parts are pursued via source-sink relation mediated by the enzymes of the apoplastic phloem unloading pathway. One of the hexoses-regulating enzymes, an extracellular invertase, was observed to be co-induced by cytokinins. However, it was further demonstrated that the extracellular invertase is required for the delaying of senescence, thus indicating the extracellular invertase as a key underlying mechanism of the delaying of senescence by cytokinins (Lara et al. 2004, Plant Cell 16:1276). Involvement of cytokinin dehydrogenase activity in the process of senescence was expected, since distinct isoforms of these cytokinin deactivating enzymes were experimentally proved to be up-regulated on the gene expression level and in enzymatic activity measurements (Šromová Lucie, diploma thesis 2006, PřF UP).

The fact that cytokinins can delay senescence is known since kinetin ($N^6$-furfurylaminopurine) was first isolated (Miller et al. 1956, J. Am. Chem. Soc. 78:1375) and tested for its anti-senescence properties on detached Xanthium leaves (Richmond & Lang 1957, Science 125:650). A variety of cytokinin derivatives were observed to delay senescence in various plant species (Zhang & Letham 1989, J. Plant Growth Regul. 8:181; Kuhnle et al. 1977, Physiol. Plant. 41:14; Eisinger 1977, Plant Physiol. 59:707; Kudryakova et al. 2001, Plant Growth Regul. 56:21). Some kinetin derivatives are already known (Zhang & Lethmm 1989, J. Plant Growth Regul. 8:181; Fox et al. 1971, Plant Phys. 47:275). We have synthesized several novel derivatives substituted at the $N^9$-position of purine with short 9-halogenalkyls and determined their anti-senescence and anti-ageing properties in different bioassays.

In an optimum concentration, the cytokinins are compounds with a stimulatory activity on cell proliferation; however, their effect is rather inhibitory in the concentrations exceeding 10 µM (Holub et al., 1998, Plant Growth Regul, 26, 109-115). It is also generally known that the cytokinin molecule acts as a negative regulator on root elongation and lateral root branching (Werner et al., 2001, Proc Natl Acad Sci USA. 98, 10487-92; Werner et al., 2003, Plant Cell, 15, 2532-50). The exogenous application of cytokinins in the concentrations exceeding 1 μM usually results in a total suppression of root growth. The aim of this invention is the preparation of novel cytokinin N9-substituted derivatives, which have unique activities in the regulation of plant growth and are not toxic to plant and animal cells at the same time.

Purine derivatives substituted in position 6 by benzyl, phenyl, furyl, furfuryl and naftyl groups (optionally further substituted), and in position 9 by lower alkyl groups, optionally containing —O— or —S— groups, fall within the general formula of GB 1,027,756 (1966) for use to promote growth and/or prevent decomposition processes in plants, but in the examples of this invention only compounds containing tetrahydropyranyl group at 9 position are disclosed, and thus the activity of compounds with lower alkyl groups in position 9 is not shown and with regard to the wide range of compounds falling into the general formula it cannot be concluded that these compounds would have the same activity. Furthermore, similar derivatives containing an optionally substituted phenyl or naftyl groups in position 6 and C1-C6 alkyl or phenyl, optionally substituted phenyl, in position 9, for regulation of plant growth fall within the general formula of EP 0155911. The activity of these derivatives is however not determined in this document; only the activity of derivatives with mesithyl substituents in position 9 is shown. With regard to the generality of the general formula and the structural differences between mesithyl and alkyl substitutents it is impossible to make any conclusions regarding the real activity of 9-alkyl substituents. Ramzayeva et al., published in Žurnal organičeskoj chimii (1988, 1090-1094) describes the procedure for substitution of 6-substituted purines by halogenalkyls. The compounds disclosed in this publication contain benzylamino or methylthio groups in position 6 and 2-chloroethyl, 2-bromoethyl and 3-chloropropyl group in position 9, respectively. Nevertheless, this paper is not mentioning any use of the above mentioned compounds.

DISCLOSURE OF THE INVENTION

The object of this invention is the use of derivatives of general formula I (I)

wherein $R_6$ is selected from the group comprising —NH-furfuryl, —NH-(4-hydroxy-3-methylbut-2-en-1-yl), —NH-(3-methylbut-2-en-1-yl), —NH-(4-hydroxy-3-methylbutyl), —NH-(4-hydroxy-1,3-dimethylbut-2-en-1-yl), —NH-(4-hydroxy-1,3-dimethylbutyl), —NH-benzyl, —NH-phenyl, wherein benzyl, furfuryl and phenyl can be unsubstituted or optionally substituted with 1 to 3 substituents selected from the group comprising hydroxy, halogen, methyl and methoxy, $R_9$ is selected from the group comprising $C_1$-$C_3$ alkyl and $C_1$-$C_3$ alkenyl wherein each of the groups is substituted with one or more halogen atoms, for the regulation of growth and development of whole plants, plant cells and/or organs.

Halogen is selected from the group containing F, Cl, Br, I.

When the compounds of this invention contain a chiral centre, then all enantiomers, mixtures of enantiomers and racemates fall within the framework of the present invention. The present invention further includes the compounds of general formula I in the form of salts with alkali metals, ammonium or amines, as well as in the form of addition salts with acids.

In a preferred embodiment, $R_9$ is $C_1$-$C_3$ alkyl or $C_1$-$C_3$ alkenyl, which is substituted on terminal carbon atom with 1 or 2 halogen atoms selected preferably from the group consisting of chlorine and bromine. More preferably, $R_9$ is selected from the group containing chloromethyl, bromomethyl, 2-chloroethyl, 2-bromoethyl, 2,2-dichloroethyl, 2,2-dibromoethyl, 3-chloropropyl, 3-bromopropyl, 3,3-dichloropropyl, 3,3-dibromopropyl, 2-chlorovinyl, 2-bromovinyl.

In another preferred embodiment, $R_6$ is selected from the group containing —NH-furfuryl, —NH-(3-methylbut-2-en-1-yl).

Particularly preferred are the 6-substituted 9-halogenalkyl derivatives of adenine of the general formula I selected from the group containing: 6-(furfurylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(2-chlorobenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(3-chlorobenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(3-fluorobenzylamino)-9-(chloromethyl, 2-chloro ethyl, 3-chloropropyl, bromomethyl, 2-bromoethyl, 3-bromopropyl, 2,2-dichloroethyl, 2-chlorovinyl, 2-bromovinyl)purine, 6-(3-hydroxybenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(3-methoxybenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(3-methylbut-2-en-1-ylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-benzylamino-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(4-hydroxy-3-methylbut-2-en-1-ylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(Z)-(4-hydroxy-3-methylbut-2-en-1-ylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(E)-(4-hydroxy-3-methylbut-2-en-1-ylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(Z)-(4-hydroxy-1,3-dimethylbut-2-en-1-ylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(E)-(4-hydroxy-1,3-dimethylbut-2-en-1-ylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(4-hydroxy-3-methylbutylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(4-hydroxy-1,3-dimethylbutylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-phenylamino-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(3-methoxyphenylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(2-methoxybenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(2-hydroxybenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(2-fluorobenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine.

A further aspect of the invention is preferably the use of 6-substituted 9-halogenalkyl adenine derivatives of the general formula I for stimulation of plant organogenesis leading to plant root growth. In comparison to cytokinins of the prior art which are known to inhibit root growth and development, the 6-substituted 9-halogenalkyl adenine derivatives of the general formula I do not have at high concentrations the negative effect on root growth or this negative effect is strongly suppressed.

Yet another aspect of the invention is preferably the use of 6-substituted 9-halogenalkyl adenine derivatives of the general formula I, for dispatching grain filling and increase of grain and fruit size of monocotyledon plants and for shortening of plant seed germination period.

Another aspect of the invention is preferably the use of 6-substituted 9-halogenalkyl adenine derivatives of the general formula I in tissue cultures for regulation of proliferation and morphogenesis and for inhibition of stress and senescence. Especially preferred are the new derivatives for use in tissue cultures because they do not exhibit the inhibitory effect on growth and division of plant cells at high concentrations and show minimum toxicity for these cells compared to classical cytokinins known in the prior art. This enables their use in broad concentration range without negative effects. The uptake of 6-substituted 9-halogenalkyl adenine derivatives of the general formula I by an intact plant does not lead to the stress responses observed with the known cytokinins which is evidenced by overexpression of stress response genes.

A further aspect of the invention is preferably the use of 6-substituted 9-halogenalkyladenine derivatives of the general formula I, for delaying chlorophyll degradation and senescence of plant tissues. This positive effect on plant growth is related to the unique effect of these derivatives on the peroxidation of membrane lipids. The 9-halogenalkyl group of these derivatives is functioning as a protective group which is able to silence the negative effect of cytokinins on the membrane degradation without any decrease of their positive effects and biological activities.

A further aspect of the invention is preferably the use of 6-substituted 9-halogenalkyl adenine derivatives of the general formula I for increasing of yield and quality of agricultural products of monocotyledonous species of plants.

This invention further preferably concerns the use of 6-substituted 9-halogenalkyl adenine derivatives of the general formula I in the production of crops, in particular monocotyledonous species. Monocot plants (Liliopsida, Monocotyledonae) are one out of two major classes of angiosperm plants. The agricultural significance of monocotyledons is absolutely fundamental for humankind. All cereal plants are members of the monocot family, including the most abundant crop species—Wheat (*Triticum aestivum*), Barley (*Hordeum vulgare*), Oat (*Avena sativa*), Panicum (*Panicum sativum*), Rice (*Oryza sativa*) and Maize (*Zea mays*), also Sugar cane (*Saccharum officinarum*) which belongs to the family of Poaceae. Other important crop plants are ranked to other monocotyledon families and subfamilies such as palms; e.g. Coconut-palm (*Cocos nucifera*) and Date-palm (*Phoenix dactylifera*); or other known crops; e.g. Banana plant (*Musa*), Pineapple (*Ananas comosus*), Asparagus (*Asparagus officinalis*), Garlic (*Allium sativum*), Onion (*Allium cepa*), Vanilla (*Vanilla*), Ginger (*Zingiber*) and many others. Many members of the monocotyledon class are also cultivated as ornamental plants for their decorative flowers and leaves, many of them originally from tropics are often used as houseplants.

A further aspect of the invention is preferably the use of 6-substituted 9-halogenalkyl adenine derivatives of the general formula I, for the preparation of preparations for cloning of plant cells, organs, plant embryonic cells and embryos.

The invention further includes the preparations for cloning of plant cells, organs, plant embryonic cells and embryos comprising at least one compounds of the general formula I and auxiliary substances.

A further object of this invention is the use of the 6-substituted 9-halogenalkyl adenine derivatives of the general formula I, for the preparation of preparations for the regulation of plant growth and development.

The invention further includes the preparations for the regulation of plant growth comprising at least one compound of the general formula I and auxiliary substances.

The compounds of the general formula I are used in unmodified form or in the form of salt, preferably together with the auxiliary substances (adjuvants) conventionally employed in the art of formulation, e.g., diluents, carriers or fillers, which are commonly used in agriculture and are known to a person skilled in the art. To this end they are conveniently formulated as concentrates of active compounds as well as suspensions and dispersions, preferably isotonic water solutions, suspensions and dispersions, diluted emulsions, soluble powders, dusts, granulates, creams, gels, oil suspensions and also encapsulations, e.g. polymeric substances. As with the type of the compositions, the methods of application, such as spraying, atomizing, dusting, scattering, coating or pouring, are chosen in accordance with the intended objectives and the prevailing circumstances. The compositions may be sterilized or contain further adjuvants of a neutral nature such as preservatives, stabilizers, wetting agents or emulgators, solubilizing agents, fertilizers, micronutrient donors or other formulations for obtaining special properties.

The compounds of the formula I can be mixed with other growth regulators, resulting in synergistic activities.

The object of this invention are derivatives of the general formula Ia, (Ia)

wherein $R_6$ is selected from the group containing —NH-furfuryl, —NH-(4-hydroxy-3-methylbut-2-en-1-yl), —NH-(3-methylbut-2-en-1-yl), —NH-(4-hydroxy-3-methylbutyl), —NH- (4-hydroxy-1,3-dimethylbut-2-en-1-yl), —NH-(4-hydroxy-1,3-dimethylbutyl), —NH-benzyl, —NH-phenyl, wherein benzyl, furfuryl and phenyl can be unsubstituted or optionally substituted with 1 to 3 substituents selected from the group comprising hydroxy, halogen, methyl and methoxy, $R_9$ is selected from the group comprising $C_1$-$C_3$ alkyl a $C_1$-$C_3$ alkenyl wherein each of the groups is substituted with one or more halogen atoms, provided that if $R_9$ is 2-chloroethyl, $R_6$ cannot be —NH-furfuryl, —NH-benzyl, if $R_9$ is 3-chloropropyl či 2-bromoethyl, $R_6$ can not be —NH-benzyl.

Preparations

The preparations comprising the compounds of formula I (active ingredients) or salts thereof and, where appropriate, one or more solid or liquid formulation auxiliary substances (adjuvants), are prepared in a manner known per se, e.g. by intimately mixing and/or grinding the active ingredients with the formulation adjuvants, e.g. solvents or solid carriers. In addition, surface-active compounds (surfactants) may also be added in the preparation of the formulations.

Depending on the nature of the compound of formula I to be formulated, suitable surface-active compounds are non-ionic, cationic and/or anionic surfactants and surfactant mixtures having good emulsifying, dispersing and wetting properties. Examples of suitable anionic, non-ionic and cationic surfactants are listed, for example, in WO 97/34485.

Also suitable in the preparation formulations containing the compounds of formula I according to the present invention are the surfactants conventionally used in formulation technology, which are described, inter alia, in "McCutcheon's Detergents and Emulsifiers Annual" MC Publishing Corp., Ridgewood N.J., 1981; Stache, H., "Tensid-Taschenbuch", Carl Hanser Verlag, Munich, 1981; and M. and J. Ash, "Encyclopedia of Surfactants", Vol. 1-3, Chemical Publishing Co., New York, 1980-81. The formulation of the preparations contains from 0.1 to 99% (w/w), especially from 0.1 to 95% (w/w), of active ingredient or active ingredient mixture comprising compounds of formula I, whereas it contains preferably from 5 to 99.9% of a solid or liquid formulation adjuvants or pharmaceutical carriers, and optionally from 0.1 to 25% of a surfactant.

Whereas commercial products are usually formulated as concentrates, the end user will normally employ diluted formulations. The compositions may also comprise further ingredients, such as stabilisers, e.g. vegetable oils or epoxidised vegetable oils (epoxidised coconut 0; 1, rapeseed oil or soybean oil), antifoams, e.g. silicone oil, preservatives, stabilizers, wetting agents or emulgators, viscosity factors, binders, tackifiers, and also fertilisers or other active ingredients. Preferred formulations have especially the following compositions: (%=percent by weight)

Emulsifiable Concentrates:
active ingredient mixture: 1 to 90%, preferably 5 to 20%
surfactant: 1 to 30%, preferably 10 to 20%
liquid carrier: 5 to 94%, preferably 60 to 85%
Dusts:
active ingredient mixture: 0.1 to 10%, preferably 0.1 to 5%
solid carrier: 99.9 to 90%, preferably 99.9 to 95%
Suspension Concentrates:
active ingredient mixture: 5 to 75%, preferably 10 to 50%
water: 94 to 24%, preferably 88 to 30%
surfactant: 1 to 40%, preferably 2 to 30%
Wettable Powders:
active ingredient mixture: 0.5 to 90%, preferably 1 to 80%
surfactant: 0.5 to 20%, preferably 1 to 15%
solid carrier: 5 to 95%, preferably 15 to 90%
Granules:
active ingredient mixture: 0.1 to 30%, preferably 0.1 to 15%
solid carrier: 99.9 to 70%, preferably 99.9 to 85%

The compositions may also comprise further ingredients, such as stabilisers, e.g. vegetable oils or epoxidised vegetable oils (epoxidised coconut oil, rapeseed oil or soybean oil), anti-foams, e.g. silicone oil, preservatives, viscosity regulators, binders, tackifiers, and also fertilisers or other active ingredients. For the use of compounds of the formula I, or of compositions comprising them, in the protection of crop plants against the damaging effects of growth regulators, various methods and techniques come into consideration, such as, for example, the following:

i) Seed Dressing a) Dressing of the seeds with a wettable powder formulation of a compound of the general formula I by shaking in a vessel until uniformly distributed over the seed surface (dry dressing). In that procedure approximately from 1 to 500 g of compound of the general formula I (4 g to 2 kg of wettable powder) are used per 100 kg of seed.

b) Dressing of the seeds with an emulsifiable concentrate of a compound of formula I or a salt thereof according to method a) (wet dressing).

c) Dressing by immersing the seeds for from 1 to 72 hours in a liquor comprising from 100 to 1000 ppm of a compound of formula I and optionally subsequently drying the seeds (immersion dressing).

Generally, the compounds of general formula I or their salts are used in the amount of from 1 to 1000 g, preferably from 5 to 250 g per 100 kg of seeds, but depending on the methodology, which also enables the addition of other active ingredients or micronutrients: the concentration limits indicated can be varied up or down (repeated dressing).

ii) Application as a Tank Mixture

A liquid formulation of a mixture of antidote and growth regulator is used (ratio by weight of the one to the other from 10:1 to 1:100), the rate of application of growth regulator being from 0.005 to 5.0 kg per hectare. Such tank mixtures are applied before or after sowing.

iii) Application to the Seed Furrow

The compounds of formula I are introduced into the open, sown seed furrow in the form of an emulsifiable concentrate, wettable powder or granules. Once the seed furrow has been covered, the growth regulator is applied in the usual manner in the pre-emergence process.

iv) Controlled Release of Active Ingredient

The compounds of formula I are applied in solution to mineral granule carriers or polymerised granules (urea/formaldehyde) and dried. If desired, it is also possible to apply a coating that allows the active ingredient to be released in metered amounts over a specific period of time (coated granules).

EXAMPLES OF CARRYING OUT THE INVENTION

The starting material for the compounds of the formula I is 6-chloropurine or 6-bromopurine. Halogenated hydrocarbons were obtained from Sigma Aldrich. Starting substituted benzylamines, not commercially available (others obtained via Sigma Aldrich or Fluorochem), were prepared from the corresponding aldehydes in the presence of suitable metal catalyst. Those having more methyl groups can preferably be prepared from the corresponding methylbenzaldehydes. Hydroxyderivatives may be prepared by demethylation of appropriate methoxyderivatives using 48% HBr in $N_2$ atmosphere.

Elemental analyses (C, H and N) were performed on an EA1108 CHN analyser (Fissons Instruments). The melting points were determined on a BÜCHI Melting Point B-540 apparatus and are uncorrected. Analytical thin layer chromatography (TLC) was carried out using silica gel 60 $WF_{254}$ plates (Merck), solvent $CHCl_3$:MeOH:conc. $NH_4OH$ (8:2:0.2, v/v/v). ES+ mass spectra were recorded using direct probe on Waters ZMD 2000 mass spectrometer. The mass monitoring interval was 10 to 1500 amu. The spectra were collected using 3.0 second cyclical scans and applying sample cone voltage 25 V at source block temperature 150° C., desolvation temperature 80° C. and desolvation gas flow rate 200 l/hour. The mass spectrometer was directly coupled to a MassLynx data system. NMR spectra were measured in a Bruker Avance AV 300 spectrometer operating at a temperature of 300 K and a frequency of 300.13 MHz ($^1H$) and 75.48 MHz ($^{13}C$), respectively. Samples were prepared by dissolving the compounds in DMSO-$d_6$. Tetramethylsilane (TMS) was used as the internal standard.

Example 1

Preparation of 6-furfurylamino-9-(2-chloroethyl)purine (1)

Kinetin (2 g, 9.3 mmol), 1-bromo-2-chloroethane (1.3 g, 9.1 mmol) and $K_2CO_3$ (2.5 g, 24 mmol) were mixed in 100 ml dimethylsulfoxide (DMSO) for 18 h. The reaction mixture was poured onto 200 ml drift ice and then extracted in ethyl acetate and dried over $Na_2SO_4$. The ethyl acetate layer was evaporated in vacuo. The pure product of white powder character was recrystallised from methanol. Yield: 80%. $^1H$ NMR (DMSO-$d_6$): 4.07 (2H, t, J=5.82), 4.52 (2H, t, J=5.82), 4.70 (2H, s (br)), 6.23 (1H, d, J=2.67), 6.35 (1H, m), 7.53 (1H, d, J=2.67), 8.22 (2H, m), 8.25 (1H, s)

Example 2

Preparation of 6-furfurylamino-9-(2-bromoethyl)purine (2)

Kinetin (2 g, 9.3 mmol) and $K_2CO_3$ (2.4 g, 23 mmol) were mixed in 100 ml dimethylformamide (DMF). 1,2-Dibromoethane (5.2 g, 27.6 mmol) was added to the reaction mixture and then it was mixed at room temperature for 12 h, humidity was regulated by $CaCl_2$ tube. Solvent was evaporated to dryness in vacuo to yellow solid and then 100 g ice was added. The mixture was shaken at least 1 h to until a white precipitate was formed. The solid was filtered off, washed with water and dried at 50° C. The product was recrystallised from methanol. Yield: 60%. $^1H$ NMR (DMSO-$d_6$): 3.95 (2H, t, J=5.91), 4.58 (2H, t, J=5.91), 4.69 (2H, s (br)), 6.23 (1H, d, J=2.94), 6.36 (1H, t, J=2.94), 7.54 (1H, d, J=2.94), 8.15 (2H, m), 8.24 (1H, s)

Example 3

Preparation of 6-[(3-methylbut-2-en-1-yl)amino]-9-(2-bromoethyl)purine (3)

Mixture of 6-[(3-methylbut-2-en-1-yl)amino]purine (2 g, 9.8 mmol), 1,2-dibromoethane (12.94 g, 6 ml, 69 mmol) and $K_2CO_3$ (2.5 g, 24 mmol) was stirred in 50 ml DMSO for 12 h. Reaction mixture was poured onto drift ice and after ice dissolution 30 ml ethyl acetate was added. Ethyl acetate layer was purified by charcoal and $SiO_2$ and then it was evaporated in vacuo. The pure product was recrystallised from methanol; yellow solid was obtained. Yield: 70%. $^1H$ NMR (DMSO-$d_6$): 1.75 (3H, s), 1.59 (3H, s), 4.12 (2H, t, J=5.76), 4.10 (2H, s (br)), 4.6 (2H, t, J=5.76), 5.3 (1H, t, J=6.57), 8.1 (1H, s (br)), 8.3 (1H, s).

Example 4

Preparation of 6-[(3-methylbut-2-en-1-yl)amino]-9-(2-chloroethyl)purine (4)

6-[(3-methylbut-2-en-1-yl)amino]purine (2 g, 9.8 mmol), 1-bromo-2-chloroethane (1.4 g, 9.8 mmol) and $K_2CO_3$ (3 g, 29 mmol) were stirred in 50 ml DMSO for 12 h. The reaction mixture was poured onto ice (200 ml) and extracted in ethylacetate (50 ml). The solid residue was recrystallized from hexane to obtain white crystals. Yield: 60%. $^1H$ NMR (DMSO-$d_6$): 1.66 (3H, s), 1.70 (3H, s), 4.06 (2H, t, J=5.76), 4.10 (2H, s (br), H12), 4.50 (2H, t, J=5.76), 5.31 (1H, t, J=6.57), 7.767 (1H, s (br)), 8.15 (1H, s), 8.20 (1H, s).

Example 5

Preparation of 6-benzylamino-9-(2-bromoethyl)purine (20)

6-Benzylaminopurine (1 g, 4.43 mmol), $K_2CO_3$ (2.45 g, 17.8 mmol) and 1,2-dibromoethane (1.15 mL, 13.3 mmol) was stirred for 16 h at room temperature under $CaCl_2$ plug in DMF (30 mL). After removal of the DMF by vacuum evaporation, the resulting material was diluted with water (30 mL) and extracted into ethyl acetate (EtOAc) (3×15 mL). The organic fractions were combined, washed with water (2×10 mL), dried over $Na_2SO_4$, purified by carbofiltration and concentrated under vacuum. The pure product was purified by flash chromatography—chloroform:methanol (9:1) was used as an eluent. Yield: 82%.

TABLE 1

Compounds prepared by the method of examples 1-5

| No | R6 | R9 | Elemental analyses calculated/found | | | ES MS |
|---|---|---|---|---|---|---|
| | | | % C | % H | % N | [M + H]+ |
| 5 | furfurylamino | chloromethyl | 50.1/49.9 | 3.8/3.8 | 26.6/26.7 | 264 |
| 6 | furfurylamino | bromomethyl | 42.9/43.0 | 3.3/3.4 | 22.7/22.5 | 309 |
| 1 | furfurylamino | 2-chloroethyl | 51.9/52.0 | 4.4/4.5 | 25.2/25.2 | 278 |
| 2 | furfurylamino | 2-bromoethyl | 44.7/44.8 | 3.8/3.9 | 21.7/21.9 | 323 |
| 7 | furfurylamino | 3-chloropropyl | 53.5/53.6 | 4.8/4.7 | 24.0/23.7 | 292 |
| 8 | furfurylamino | 3-bromopropyl | 46.4/46.1 | 4.2/4.2 | 20.8/21.1 | 337 |
| 9 | furfurylamino | 2-chlorovinyl | 52.3/52.1 | 3.7/3.6 | 25.4/25.2 | 276 |
| 10 | furfurylamino | 2-bromovinyl | 45.0/45.1 | 3.2/3.2 | 21.9/21.6 | 321 |
| 11 | furfurylamino | 2,2-dichloroethyl | 46.2/46.5 | 3.6/3.4 | 22.4/22.7 | 313 |
| 12 | (3-methylbut-2-en-1-yl)amino | chloromethyl | 52.5/52.4 | 5.6/5.5 | 27.8/27.5 | 252 |
| 13 | (3-methylbut-2-en-1-yl)amino | bromomethyl | 44.6/44.9 | 4.8/4.6 | 23.7/24.0 | 297 |
| 3 | (3-methylbut-2-en-1-yl)amino | 2-bromoethyl | 46.5/46.3 | 5.2/5.2 | 22.6/22.1 | 310 |
| 4 | (3-methylbut-2-en-1-yl)amino | 2-chloroethyl | 54.2/54.6 | 6.1/6.2 | 26.4/26.2 | 266 |
| 14 | (3-methylbut-2-en-1-yl)amino | 3-bromopropyl | 48.2/48.2 | 5.6/5.6 | 21.6/21.3 | 325 |
| 15 | (3-methylbut-2-en-1-yl)amino | 3-chloropropyl | 55.8/56.0 | 6.5/6.1 | 25.0/24.6 | 280 |
| 16 | (3-methylbut-2-en-1-yl)amino | 2-chlorovinyl | 54.7/54.3 | 5.4/5.3 | 26.6/26.3 | 264 |
| 17 | (3-methylbut-2-en-1-yl)amino | 2-bromovinyl | 46.8/46.7 | 4.6/4.3 | 22.7/22.4 | 309 |
| 18 | (3-methylbut-2-en-1-yl)amino | 2,2-dichloroethyl | 48.0/48.4 | 5.0/5.2 | 23.3/23.0 | 301 |
| 19 | benzylamino | chloromethyl | 57.0/58.3 | 4.4/4.5 | 25.6/25.7 | 274 |
| 20 | benzylamino | 2-chloroethyl | 58.4/58.7 | 4.9/5.0 | 24.3/24.2 | 288 |
| 21 | benzylamino | 3-chloropropyl | 59.7/60.1 | 5.3/5.5 | 23.2/23.5 | 302 |
| 22 | benzylamino | bromomethyl | 49.1/49.1 | 3.8/3.9 | 22.0/21.8 | 319 |
| 23 | benzylamino | 2-bromoethyl | 50.6/50.5 | 4.3/4.2 | 21.1/21.4 | 333 |
| 24 | benzylamino | 3-bromopropyl | 52.0/52.3 | 4.7/4.9 | 20.2/20.5 | 347 |
| 25 | benzylamino | 2-chlorovinyl | 58.9/59.8 | 4.2/4.1 | 24.5/24.2 | 286 |
| 26 | benzylamino | 2-bromovinyl | 50.9/50.7 | 3.7/3.6 | 21.2/21.5 | 331 |
| 27 | benzylamino | 2,2-dichloroethyl | 52.2/52.5 | 4.1/4.3 | 21.7/21.4 | 323 |
| 28 | phenylamino | chloromethyl | 55.5/55.1 | 3.9/3.7 | 27.0/27.3 | 260 |
| 29 | phenylamino | 2-chloroethyl | 57.0/57.1 | 4.4/4.5 | 25.6/25.4 | 274 |
| 30 | phenylamino | 3-chloropropyl | 58.4/58.4 | 4.9/4.9 | 24.3/24.2 | 288 |
| 31 | phenylamino | bromomethyl | 47.4/47.8 | 3.3/3.5 | 23.0/23.2 | 305 |
| 32 | phenylamino | 2-bromoethyl | 49.1/49.2 | 3.8/3.9 | 22.0/22.3 | 319 |
| 33 | phenylamino | 3-bromopropyl | 50.6/50.4 | 4.3/4.5 | 21.1/21.4 | 333 |
| 34 | phenylamino | 2-bromovinyl | 49.4/49.1 | 3.2/3.0 | 22.2/21.8 | 317 |
| 35 | phenylamino | 2-chlorovinyl | 57.5/57.9 | 3.7/3.9 | 25.8/26.0 | 272 |
| 36 | phenylamino | 2,2-dichloroethyl | 50.7/50.5 | 3.6/3.7 | 22.7/22.8 | 309 |
| 37 | 3-methoxy-benzylamino | chloromethyl | 55.4/55.2 | 4.7/4.7 | 23.1/23.4 | 304 |
| 38 | 3-methoxy-benzylamino | 2-chloroethyl | 56.7/56.4 | 5.1/5.2 | 22.0/22.1 | 318 |
| 39 | 3-methoxy-benzylamino | 3-chloropropyl | 57.9/58.0 | 5.5/5.2 | 21.1/21.5 | 332 |
| 40 | 3-methoxy-benzylamino | bromomethyl | 48.3/48.3 | 4.1/4.2 | 20.1/20.0 | 349 |
| 41 | 3-methoxy-benzylamino | 2-bromoethyl | 49.7/49.6 | 4.5/4.4 | 19.3/19.1 | 363 |
| 42 | 3-methoxy-benzylamino | 3-bromopropyl | 51.1/51.3 | 4.8/4.9 | 18.6/19.0 | 377 |
| 43 | 3-methoxy-benzylamino | 2-chlorovinyl | 57.1/57.3 | 4.5/4.5 | 22.2/22.6 | 316 |
| 44 | 3-methoxy-benzylamino | 2-bromovinyl | 50.0/49.7 | 3.9/3.6 | 19.4/19.1 | 361 |
| 45 | 3-methoxy-benzylamino | 2,2-dichloroethyl | 51.2/51.5 | 4.3/4.3 | 19.9/20.1 | 353 |
| 46 | 3-hydroxy-benzylamino | chloromethyl | 53.9/54.2 | 4.2/4.3 | 24.2/24.6 | 290 |
| 47 | 3-hydroxy-benzylamino | 2-chloroethyl | 55.4/55.3 | 4.7/4.8 | 23.1/23.2 | 304 |
| 48 | 3-hydroxy-benzylamino | 3-chloropropyl | 56.7/56.4 | 5.1/5.0 | 22.0/21.8 | 318 |
| 49 | 3-hydroxy-benzylamino | bromomethyl | 46.7/46.8 | 3.6/3.6 | 21.0/21.3 | 335 |
| 50 | 3-hydroxy-benzylamino | 2-bromoethyl | 48.3/48.0 | 4.1/4.4 | 20.1/20.5 | 349 |

TABLE 1-continued

Compounds prepared by the method of examples 1-5

| No | R6 | R9 | Elemental analyses calculated/found | | | ES MS |
|---|---|---|---|---|---|---|
| | | | % C | % H | % N | [M + H]+ |
| 51 | 3-hydroxy-benzylamino | 3-bromopropyl | 49.7/49.5 | 4.5/4.4 | 19.3/19.1 | 363 |
| 52 | 3-hydroxy-benzylamino | 2-chlorovinyl | 55.7/55.8 | 4.0/4.1 | 23.2/23.5 | 302 |
| 53 | 3-hydroxy-benzylamino | 2-bromovinyl | 48.6/48.4 | 3.5/3.7 | 20.2/21.9 | 347 |
| 54 | 3-hydroxy-benzylamino | 2,2-dichloroethyl | 49.7/49.8 | 3.9/4.0 | 20.7/20.8 | 339 |
| 55 | 2-methoxy-benzylamino | chloromethyl | 55.4/55.1 | 4.7/4.4 | 23.1/22.8 | 304 |
| 56 | 2-methoxy-benzylamino | 2-chloroethyl | 56.7/56.8 | 5.1/5.2 | 22.0/22.1 | 318 |
| 57 | 2-methoxy-benzylamino | 3-chloropropyl | 57.9/57.8 | 5.5/5.5 | 21.1/21.0 | 332 |
| 58 | 2-methoxybenzylamino | bromomethyl | 48.3/48.2 | 4.1/4.0 | 20.1/20.3 | 349 |
| 59 | 2-methoxy-benzylamino | 2-bromoethyl | 49.7/50.0 | 4.5/4.7 | 19.3/19.4 | 363 |
| 60 | 2-methoxy-benzylamino | 3-bromopropyl | 51.1/51.4 | 4.8/4.9 | 18.6/18.4 | 377 |
| 61 | 2-methoxy-benzylamino | 2-bromovinyl | 50.0/49.9 | 3.9/3.9 | 19.4/19.4 | 361 |
| 62 | 2-methoxy-benzylamino | 2-chlorovinyl | 57.1/57.4 | 4.5/4.6 | 22.2/22.6 | 316 |
| 63 | 2-methoxy-benzylamino | 2,2-dichloroethyl | 51.2/51.0 | 4.3/4.5 | 19.9/20.3 | 353 |
| 64 | 2-hydroxy-benzylamino | chloromethyl | 53.9/53.7 | 4.2/4.1 | 24.2/24.1 | 290 |
| 65 | 2-hydroxy-benzylamino | 2-chloroethyl | 55.4/55.3 | 4.7/4.8 | 23.1/23.2 | 304 |
| 66 | 2-hydroxy-benzylamino | 3-chloropropyl | 56.7/56.8 | 5.1/5.1 | 22.0/21.9 | 318 |
| 67 | 2-hydroxy-benzylamino | bromomethyl | 46.7/46.8 | 3.6/3.7 | 21.0/21.3 | 335 |
| 68 | 2-hydroxy-benzylamino | 2-bromoethyl | 48.3/48.1 | 4.1/4.3 | 20.1/20.4 | 349 |
| 69 | 2-hydroxy-benzylamino | 3-bromopropyl | 49.7/49.3 | 4.5/4.2 | 19.3/19.5 | 363 |
| 70 | 2-hydroxy-benzylamino | 2-chlorovinyl | 55.7/56.0 | 4.0/4.1 | 23.2/23.7 | 302 |
| 71 | 2-hydroxy-benzylamino | 2-bromovinyl | 48.6/48.9 | 3.5/3.7 | 20.2/20.1 | 347 |
| 72 | 2-hydroxy-benzylamino | 2,2-dichorethyl | 49.7/49.6 | 3.9/3.9 | 20.7/20.9 | 339 |
| 73 | 2-fluoro-benzylamino | chloromethyl | 53.5/53.4 | 3.8/3.8 | 24.0/23.7 | 292 |
| 74 | 2-fluoro-benzylamino | 2-chloroethyl | 55.0/55.1 | 4.3/4.3 | 22.9/23.1 | 306 |
| 75 | 2-fluoro-benzylamino | 3-chloropropyl | 56.3/56.7 | 4.7/4.9 | 21.9/21.9 | 320 |
| 76 | 2-fluoro-benzylamino | bromomethyl | 46.5/46.1 | 3.3/3.0 | 20.8/20.6 | 337 |
| 77 | 2-fluoro-benzylamino | 2-bromoethyl | 48.0/48.2 | 3.7/3.8 | 20.0/20.4 | 351 |
| 78 | 2-fluoro-benzylamino | 3-bromopropyl | 49.5/49.6 | 4.2/4.2 | 19.2/19.6 | 365 |
| 79 | 2-fluoro-benzylamino | 2-bromovinyl | 48.3/48.3 | 3.2/3.1 | 20.1/19.8 | 349 |
| 80 | 2-fluoro-benzylamino | 2-chlorovinyl | 55.4/55.6 | 3.7/3.8 | 23.1/23.4 | 304 |
| 81 | 2-fluoro-benzylamino | 2,2-dichloroethyl | 49.4/49.1 | 3.6/3.4 | 20.6/20.2 | 341 |
| 82 | 3-fluoro-benzylamino | chloromethyl | 53.5/53.7 | 3.8/4.0 | 24.0/24.3 | 292 |
| 83 | 3-fluoro-benzylamino | 2-chloroethyl | 55.0/55.2 | 4.3/4.3 | 22.9/23.1 | 306 |
| 84 | 3-fluoro-benzylamino | 3-chloropropyl | 56.3/56.5 | 4.7/4.7 | 21.9/22.2 | 320 |
| 85 | 3-fluoro-benzylamino | bromomethyl | 46.5/46.1 | 3.3/2.9 | 20.8/20.5 | 337 |
| 86 | 3-fluoro-benzylamino | 2-bromoethyl | 48.0/48.0 | 3.7/3.7 | 20.0/20.2 | 351 |
| 87 | 3-fluoro-benzylamino | 3-bromopropyl | 49.5/49.4 | 4.2/4.2 | 19.2/19.5 | 365 |

TABLE 1-continued

Compounds prepared by the method of examples 1-5

| No | R6 | R9 | Elemental analyses calculated/found | | | ES MS |
|---|---|---|---|---|---|---|
| | | | % C | % H | % N | [M + H]+ |
| 88 | 3-fluoro-benzylamino | 2-chlorovinyl | 55.4/55.5 | 3.7/3.7 | 23.1/23.4 | 304 |
| 89 | 3-fluoro-benzylamino | 2-bromovinyl | 48.3/48.2 | 3.2/3.0 | 20.1/19.8 | 349 |
| 90 | 3-fluoro-benzylamino | 2,2-dichloroethyl | 49.4/49.9 | 3.6/3.6 | 20.6/20.8 | 341 |
| 91 | 2-chloro-benzylamino | chloromethyl | 50.7/50.8 | 3.6/3.9 | 22.7/23.1 | 309 |
| 92 | 2-chloro-benzylamino | 2-chloroethyl | 52.2/51.9 | 4.1/3.8 | 21.7/21.5 | 323 |
| 93 | 2-chloro-benzylamino | 3-chloropropyl | 53.6/53.2 | 4.5/4.4 | 20.8/20.5 | 337 |
| 94 | 2-chloro-benzylamino | bromomethyl | 44.3/44.1 | 3.1/3.0 | 19.9/19.7 | 353 |
| 95 | 2-chloro-benzylamino | 2-bromoethyl | 45.9/46.2 | 3.6/3.7 | 19.1/19.3 | 367 |
| 96 | 2-chloro-benzylamino | 3-bromopropyl | 47.3/47.5 | 4.0/4.2 | 18.4/18.7 | 381 |
| 97 | 2-chloro-benzylamino | 2-chlorovinyl | 52.5/52.2 | 3.5/3.3 | 21.9/21.6 | 321 |
| 98 | 2-chloro-benzylamino | 2-bromovinyl | 46.1/46.3 | 3.0/3.1 | 19.2/19.4 | 365 |
| 99 | 2-chloro-benzylamino | 2,2-dichloroethyl | 47.2/47.3 | 3.4/3.4 | 19.6/19.9 | 357 |
| 100 | 3-chloro-benzylamino | chloromethyl | 50.7/50.5 | 3.6/3.3 | 22.7/22.4 | 309 |
| 101 | 3-chloro-benzylamino | 2-chloroethyl | 52.2/52.2 | 4.1/4.0 | 21.7/22.0 | 322 |
| 102 | 3-chloro-benzylamino | 3-chloropropyl | 53.6/53.7 | 4.5/4.5 | 20.8/21.0 | 337 |
| 103 | 3-chloro-benzylamino | bromomethyl | 44.3/44.3 | 3.1/3.0 | 19.9/197 | 353 |
| 104 | 3-chloro-benzylamino | 2-bromoethyl | 45.9/45.9 | 3.6/3.6 | 19.1/19.0 | 367 |
| 105 | 3-chloro-benzylamino | 3-bromopropyl | 47.3/47.1 | 4.0/3.8 | 18.4/18.1 | 381 |
| 106 | 3-chloro-benzylamino | 2-chlorovinyl | 52.5/53.7 | 3.5/3.8 | 21.9/22.2 | 321 |
| 107 | 3-chloro-benzylamino | 2-bromovinyl | 46.1/46.3 | 3.0/3.0 | 19.2/19.6 | 365 |
| 108 | 3-chloro-benzylamino | 2,2-dichloroethyl | 47.2/47.3 | 3.4/3.4 | 19.6/19.8 | 357 |
| 109 | (Z)-(4-hydroxy-3-methylbut-2-en-1-yl)amino | bromomethyl | 42.3/42.3 | 4.5/4.2 | 22.4/22.1 | 313 |
| 110 | (Z)-(4-hydroxy-3-methylbut-2-en-1-yl)amino | 2-bromoethyl | 44.2/44.2 | 4.9/5.1 | 21.5/21.5 | 327 |
| 111 | (Z)-(4-hydroxy-3-methylbut-2-en-1-yl)amino | 3-bromopropyl | 45.9/45.7 | 5.3/5.1 | 20.6/20.3 | 341 |
| 112 | (Z)-(4-hydroxy-3-methylbut-2-en-1-yl)amino | chloromethyl | 49.4/49.7 | 5.3/5.5 | 26.2/25.4 | 268 |
| 113 | (Z)-(4-hydroxy-3-methylbut-2-en-1-yl)amino | 2-chloroethyl | 51.2/51.2 | 5.7/5.7 | 24.9/25.1 | 282 |
| 114 | (Z)-(4-hydroxy-3-methylbut-2-en-1-yl)amino | 3-chloropropyl | 52.8/52.8 | 6.1/6.3 | 23.7/24.0 | 296 |
| 115 | (Z)-(4-hydroxy-3-methylbut-2-en-1-yl)amino | 2-chlorovinyl | 51.5/51.8 | 5.0/5.3 | 25.0/25.4 | 280 |
| 116 | (Z)-(4-hydroxy-3-methylbut-2-en-1-yl)amino | 2-bromovinyl | 44.5/44.7 | 4.4/4.5 | 21.6/21.9 | 325 |
| 117 | (Z)-(4-hydroxy-3-methylbut-2-en-1-yl)amino | 2,2-dichloroethyl | 45.6/45.4 | 4.8/4.8 | 22.2/21.9 | 317 |
| 118 | (E)-(4-hydroxy-3-methylbut-2-en-1-yl)amino | bromomethyl | 42.3/42.1 | 4.5/4.3 | 22.4/22.1 | 313 |

TABLE 1-continued

Compounds prepared by the method of examples 1-5

| No | R6 | R9 | Elemental analyses calculated/found | | | ES MS |
|---|---|---|---|---|---|---|
| | | | % C | % H | % N | [M + H]+ |
| 119 | (E)-(4-hydroxy-3-methylbut-2-en-1-yl)amino | 2-bromoethyl | 44.2/44.2 | 4.9/5.1 | 21.5/21.5 | 327 |
| 120 | (E)-(4-hydroxy-3-methylbut-2-en-1-yl)amino | 3-bromopropyl | 45.9/45.8 | 5.3/5.1 | 20.6/20.4 | 341 |
| 121 | (E)-(4-hydroxy-3-methylbut-2-en-1-yl)amino | chloromethyl | 49.4/49.5 | 5.3/5.4 | 26.2/26.4 | 268 |
| 122 | (E)-(4-hydroxy-3-methylbut-2-en-1-yl)amino | 2-chloroethyl | 51.2/51.4 | 5.7/5.9 | 24.9/25.1 | 282 |
| 123 | (E)-(4-hydroxy-3-methylbut-2-en-1-yl)amino | 3-chloropropyl | 52.8/52.4 | 6.1/6.0 | 23.7/23.4 | 296 |
| 124 | (E)-(4-hydroxy-3-methylbut-2-en-1-yl)amino | 2-chlorovinyl | 51.5/51.4 | 5.0/5.0 | 25.0/24.6 | 280 |
| 125 | (E)-(4-hydroxy-3-methylbut-2-en-1-yl)amino | 2-bromovinyl | 44.5/44.7 | 4.4/4.5 | 21.6/21.8 | 325 |
| 126 | (E)-(4-hydroxy-3-methylbut-2-en-1-yl)amino | 2,2-dichloroethyl | 45.6/45.7 | 4.8/5.0 | 22.2/22.6 | 317 |
| 127 | (Z)-(4-hydroxy-1,3-dimethylbut-2-en-1-yl)amino | chloromethyl | 51.2/51.5 | 5.7/5.6 | 24.9/24.7 | 282 |
| 128 | (Z)-(4-hydroxy-1,3-dimethylbut-2-en-1-yl)amino | 2-chloroethyl | 52.8/52.9 | 6.1/6.1 | 23.7/23.9 | 296 |
| 128 | (Z)-(4-hydroxy-1,3-dimethylbut-2-en-1-yl)amino | 3-chloropropyl | 54.3/54.0 | 6.5/6.2 | 22.6/22.3 | 310 |
| 129 | (Z)-(4-hydroxy-1,3-dimethylbut-2-en-1-yl)amino | bromomethyl | 44.2/44.5 | 4.9/4.7 | 21.5/21.3 | 327 |
| 130 | (Z)-(4-hydroxy-1,3-dimethylbut-2-en-1-yl)amino | 2-bromoethyl | 45.9/45.7 | 5.3/5.1 | 20.6/20.4 | 341 |
| 131 | (Z)-(4-hydroxy-1,3-dimethylbut-2-en-1-yl)amino | 3-bromopropyl | 47.5/47.4 | 5.7/5.7 | 19.8/19.6 | 355 |
| 132 | (Z)-(4-hydroxy-1,3-dimethylbut-2-en-1-ylamino) | 2-chlorovinyl | 53.2/53.5 | 5.5/5.4 | 23.8/24.0 | 294 |
| 133 | (Z)-(4-hydroxy-1,3-dimethylbut-2-en-1-ylamino) | 2-bromovinyl | 46.2/46.1 | 4.8/5.0 | 20.7/21.0 | 339 |
| 134 | (Z)-(4-hydroxy-1,3-dimethylbut-2-en-1-yl)amino | 2,2-dichloroethyl | 47.3/47.1 | 5.2/5.3 | 21.2/21.0 | 331 |
| 135 | (E)-(4-hydroxy-1,3-dimethylbut-2-en-1-yl)amino | chloromethyl | 51.2/51.4 | 5.7/5.9 | 24.9/24.6 | 282 |
| 136 | (E)-(4-hydroxy-1,3-dimethylbut-2-en-1-yl)amino | 2-chloroethyl | 52.8/52.5 | 6.1/5.9 | 23.7/23.4 | 296 |
| 137 | (E)-(4-hydroxy-1,3-dimethylbut-2-en-1-ylamino) | 3-chloropropyl | 54.3/54.5 | 6.5/6.7 | 22.6/22.8 | 310 |
| 138 | (E)-(4-hydroxy-1,3-methylbut-2-en-1-yl)amino | bromomethyl | 44.2/44.1 | 4.9/4.8 | 21.5/21.3 | 327 |
| 139 | (E)-(4-hydroxy-1,3-dimethylbut-2-en-1-yl)amino | 2-bromoethyl | 45.9/46.2 | 5.3/5.5 | 20.6/20.9 | 341 |
| 140 | (E)-(4-hydroxy-1,3-dimethylbut-2-en-1-yl)amino | 3-bromopropyl | 47.5/47.3 | 5.7/5.3 | 19.8/19.4 | 355 |
| 141 | (E)-(4-hydroxy-1,3-dimethylbut-2-en-1-yl)amino | 2-chlorovinyl | 53.2/53.6 | 5.5/5.8 | 23.8/24.0 | 294 |

TABLE 1-continued

Compounds prepared by the method of examples 1-5

| No | R6 | R9 | Elemental analyses calculated/found | | | ES MS |
|---|---|---|---|---|---|---|
| | | | % C | % H | % N | [M + H]+ |
| 142 | (E)-(4-hydroxy-1,3-dimethylbut-2-en-1-yl)amino | 2-bromovinyl | 46.2/46.1 | 4.8/4.6 | 20.7/20.5 | 339 |
| 143 | (E)-(4-hydroxy-1,3-dimethylbut-2-en-1-yl)amino | 2,2-dichloroethyl | 47.3/47.6 | 5.2/5.4 | 21.2/21.5 | 331 |
| 144 | 3-methoxy-phenylamino | chloromethyl | 53.9/53.8 | 4.2/4.2 | 24.2/24.1 | 290 |
| 145 | 3-methoxy-phenylamino | 2-chloroethyl | 55.4/55.5 | 4.7/4.6 | 23.1/23.2 | 304 |
| 146 | 3-methoxy-phenylamino | bromomethyl | 46.7/46.9 | 3.6/3.9 | 21.0/21.4 | 335 |
| 147 | 3-methoxy-phenylamino | 2-bromoethyl | 48.3/48.7 | 4.1/4.3 | 20.1/20.2 | 349 |
| 148 | 3-methoxy-phenylamino | 3-bromopropyl | 49.7/49.6 | 4.5/4.5 | 19.3/19.1 | 363 |
| 149 | 3-methoxy-phenylamino | 3-chloropropyl | 56.7/56.4 | 5.1/5.2 | 22.0/22.1 | 318 |
| 150 | 3-methoxy-phenylamino | 2-chlorovinyl | 55.7/55.8 | 4.0/4.2 | 23.2/23.5 | 302 |
| 151 | 3-methoxy-phenylamino | 2-bromovinyl | 48.6/48.9 | 3.5/3.8 | 20.2/20.5 | 347 |
| 152 | 3-methoxy-phenylamino | 2,2-dichloroethyl | 49.7/49.9 | 3.9/3.8 | 20.7/20.4 | 339 |
| 153 | 4-hydroxy-3-methylbutylamino | chloromethyl | 49.0/48.2 | 6.0/5.8 | 26.0/26.3 | 270 |
| 154 | 4-hydroxy-3-methylbutylamino | 2-chloroethyl | 50.8/50.5 | 6.4/6.1 | 24.7/24.3 | 284 |
| 155 | 4-hydroxy-3-methylbutylamino | 3-chloropropyl | 52.8/52.7 | 6.1/6.0 | 23.7/23.6 | 296 |
| 156 | 4-hydroxy-3-methylbutylamino | bromomethyl | 42.1/42.3 | 5.1/5.4 | 22.3/22.5 | 315 |
| 157 | 4-hydroxy-3-methylbutylamino | 2-bromoethyl | 43.9/44.0 | 5.5/5.6 | 21.3/21.4 | 329 |
| 158 | 4-hydroxy-3-methylbutylamino | 3-bropropyl | 45.6/45.8 | 5.9/6.0 | 20.5/20.2 | 343 |
| 159 | 4-hydroxy-3-methylbutylamino | 2-chlorovinyl | 51.2/51.1 | 5.7/5.9 | 24.9/25.2 | 282 |
| 160 | 4-hydroxy-3-methylbutylamino | 2-bromovinyl | 44.2/44.4 | 4.9/5.1 | 21.5/21.8 | 327 |
| 161 | 4-hydroxy-3-methylbutylamino | 2,2-dichloroethyl | 45.3/45.1 | 5.4/5.3 | 22.0/21.7 | 319 |
| 162 | 4-hydroxy-1,3-dimethylbutylamino | chloromethyl | 50.8/50.7 | 6.4/6.3 | 24.7/24.5 | 284 |
| 163 | 4-hydroxy-1,3-dimethylbutylamino | 2-chloroethyl | 52.4/52.3 | 6.8/6.7 | 23.5/23.1 | 298 |
| 164 | 4-hydroxy-1,3-dimethylbutylamino | 3-chloropropyl | 53.9/54.2 | 7.1/7.4 | 22.5/22.7 | 312 |
| 165 | 4-hydroxy-1,3-dimethylbutylamino | bromomethyl | 43.9/43.7 | 5.5/5.3 | 21.3/21.1 | 329 |
| 166 | 4-hydroxy-1,3-dimethylbutylamino | 2-bromoethyl | 45.6/45.8 | 5.9/6.1 | 20.5/20.7 | 343 |
| 167 | 4-hydroxy-1,3-dimethylbutylamino | 3-bromopropyl | 47.2/47.0 | 6.2/6.2 | 19.7/19.4 | 357 |
| 168 | 4-hydroxy-1,3-dimethylbutylamino | 2-chlorovinyl | 52.8/52.7 | 6.1/6.1 | 23.7/23.9 | 296 |
| 169 | 4-hydroxy-1,3-dimethylbutylamino | 2-bromovinyl | 45.9/45.7 | 5.3/5.2 | 20.6/20.4 | 341 |
| 170 | 4-hydroxy-1,3-dimethylbutylamino | 2,2-dichloroethyl | 47.0/46.9 | 5.8/5.7 | 21.1/21.4 | 333 |

Example 6

Testing of the Effect of Novel Compounds on Plant Cell Division

Figure 1:
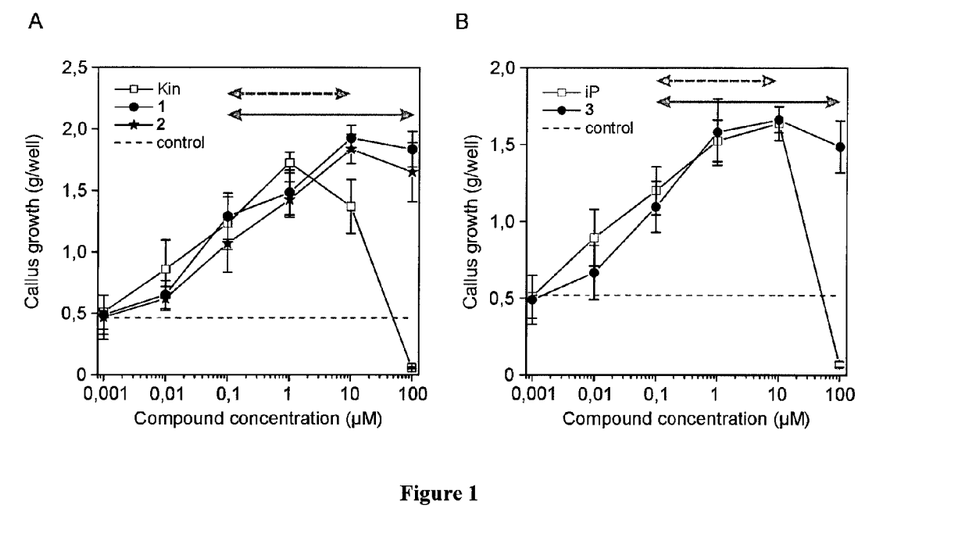
FIG. 1 shows the effect of the novel compounds on cytokinin-dependent callus growth. A, effect of kinetin and N9-substituted derivatives of kinetin; B, effect of iP and N9-substituted derivatives of iP. Red arrows indicate concentration range in which the novel compounds (solid line), or kinetin and iP (dashed line) stimulate callus growth to the level higher than 50% of its maximal growth induced by parent classical cytokinin. Error bars show SD (n=6).

Stimulatory effect of newly prepared derivatives was tested using cytokinin-dependent tobacco callus. The cytokinin-dependent tobacco callus *Nicotiana tabacum* L. cv. Wisconsin 38 was maintained at 25° C. in darkness on modified MS medium, containing per 1 liter: 4 μmol of nicotinic acid, 2.4 μmol of pyridoxine hydrochloroide, 1.2 μmol of thiamine, 26.6 μmol of glycine, 1.37 μmol of glutamine, 1.8 μmol of myo-inositol, 30 g of sucrose, 8 g of agar, 5.37 μmol of NAA and 0.5 μmol of the compound tested. Subcultivation was carried out every three weeks. Fourteen days before the bioassay, the callus tissue was transferred to the media without the compound tested. The biological activity was determined from the increase of the fresh callus weight after four weeks of cultivation. Six replicates were prepared for each concentration of the compound tested and the entire test was repeated twice. In each experiment activities of the novel compounds were tested and compared with activity of their N9-unsubstituted parent cytokinins Kin and iP, which are known to be highly active cytokinins. The compounds to be tested were dissolved in dimethylsulfoxide (DMSO) and the solution brought up to $10^{-3}$ M with distilled water. This stock solution was further diluted with the respective media used for the biotest to a concentration ranging from $10^{-8}$ M to $10^{-4}$ M. The final concentration of DMSO in the medium did not exceed 0.2% and therefore did not affect the biological activity in the assay system used. From the obtained data, the concentration with the highest activity was selected for each compound tested. Relative activity of the compound at this concentration was calculated (Table 2). The activity obtained for $10^{-6}$ M of the N9-unsubstituted parent cytokinins Kin and $10^{-5}$ M iP, respectively, was postulated as 100% biological activity. Compounds functioning as cytokinins should exhibit stimulatory effect on cell division of plant cells. The results in Table 2 show that the newly prepared substituted derivatives of the general formula I showed stronger cytokinin activity in the callus bioassay than classical cytokinins Kin and iP. For comparison, compounds bearing halogenbutyl substituent in position 9 were prepared and tested. Their activity is significantly lower than that of the derivatives of the present invention.

nins. As shown in FIG. 1 N9-alkyl substitution prevented the typical cytokinin inhibitory effect on the cell proliferation in the high concentrations exceeding 10 μM and even in the highest concentration applied (100 μM) the compounds 1, 2 and 4 still kept their stimulatory effect, whereas their N9-unsubstituted parent cytokinins (Kin, iP) inhibited strongly the callus growth (FIG. 1). The tested 9-(4-chlorobutyl) and 9-(4-bromobutyl) kinetin derivatives have shown similar inhibition activity as the N9-unsubstituted parent cytokinins.

The novel compounds of the general formula I are thus capable of stimulation of cell proliferation in much higher concentration range than classical cytokinins and in contrast to them do not have the negative (inhibitory) effect when applied in the high concentrations.

Example 8

Anti-Senescent Activity of Novel Compounds Tested in Senescent Bioassay on Wheat Leaf Segments in the Dark Conditions Seeds of winter wheat, *Triticum aestivum* cv. Hereward, were washed under running water for 24 hours and then sown on vermiculite soaked with Knop's solution. They were placed in the growth chamber at 25° C. with a 16/8 h light period at 50 μmol·m$^{-2}$·s$^{-1}$. After 7 days, the first leaf was fully developed and the second leaf had started to grow. A tip

TABLE 2

The effect of novel compounds on the growth of cytokinin-dependent tobacco callus *Nicotiana tabacum* L. cv. Wisconsins 38

| No | Tested compound | concentration with highest activity (mol. l$^{-1}$) | activity (%) [10$^{-6}$ mol. l$^{-1}$ Kin = 100%] | activity (%) [10$^{-5}$ mol. l$^{-1}$ iP = 100%] |
|---|---|---|---|---|
|  | 6-furfurylaminopurine (Kin) | 10$^{-6}$ | 100 |  |
| 1 | 6-furfurylamino-9-(2-chloroethyl)purine | 10$^{-5}$ | 120 (±6) |  |
| 2 | 6-furfurylamino-9-(2-bromoethyl)purine | 10$^{-5}$ | 110 (±3) |  |
|  | 6-(3-methylbut-2-en-1-yl)aminopurine (iP) | 10$^{-5}$ |  | 100 |
| 3 | 6-((3-methylbut-2-en-1-yl)amino)-9-(2-bromoethyl)purine | 10$^{-5}$ |  | 103 (±4) |
| 4 | 6-((3-methylbut-2-en-1-yl)amino)-9-(2-chloroethyl)purine | 10$^{-5}$ |  | 112 (±7) |
| 38 | 3-methoxy-benzylamino-9-(2-chloroethyl)purine | 10$^{-5}$ | 106 (±5) |  |
| 47 | 3-hydroxy-benzylamino-9-(2-chloroethyl)purine | 10$^{-5}$ | 111 (±2) |  |
| 136 | 6-(E)-(4-hydroxy-1,3-dimethylbut-2-en-1-ylamino)-9-(2-chloroethyl)purine | 10$^{-5}$ | 115 (±7) |  |
|  | 6-furfurylamino-9-(4-chlorobutyl)purine | 10$^{-4}$ | 62 (±7) |  |
|  | 6-furfurylamino-9-(4-bromobutyl)purine | 10$^{-4}$ | 45 (±8) |  |

Example 7

Stimulation of Cell Proliferation in High Concentrations

Cytokinins are known to have stimulatory effects on cell proliferation in their optimal concentrations, however typically in the concentrations exceeding 10 μM their effect on cell division turns into inhibitory (Holub et al., *Plant Growth Regul.* 26, 109-115, 1998). Therefore the effect of the high concentrations of the newly prepared derivatives was tested using cytokinin-dependent tobacco callus described in Example 6. The novel compounds 1, 2 and 4 were tested in high concentrations (1-100 μM) and the activities were compared with activities of their N9-unsubstituted parent cytokisection of the first leaf, approximately 35 mm long, was removed from 5 seedlings and trimmed slightly to a combined weight of 100 mg. The basal ends of the five leaf tips were placed in the wells of a microtiter polystyrene plate containing 150 μL of the tested derivative solution each. The entire plate was inserted into a plastic box lined with paper tissues soaked in distilled water to prevent leaf sections from drying out. After 96 h incubation in the dark at 25° C., the leaves were removed and chlorophyll extracted by heating at 80° C. for 10 min in 5 mL of 80% ethanol (v/v). The sample volume was then restored to 5 mL by the addition of 80% ethanol (v/v). The absorbance of the extract was recorded at 665 nm. In addition, chlorophyll extracts from fresh leaves and leaf tips incubated in deionised water were measured. The results are means of five replicates and the entire test was repeated twice.

In each experiment activities of the novel compounds were tested and compared with activity of their N9-unsubstituted parent cytokinin Kin, which is known to be highly active cytokinin. The compounds to be tested were dissolved in dimethylsulfoxide (DMSO) and the solution brought up to $10^{-3}$ M with distilled water. This stock solution was further diluted with the respective media used for the biotest to a concentration ranging from $10^{-8}$ M to $10^{-4}$ M. The final concentration of DMSO did not exceed 0.2% and therefore did not affect the biological activity in the assay system used. The activity obtained for $10^{-4}$ M Kin was postulated as 100%.

The compound functioning as cytokinins should exhibit positive effect on delaying of senescence in wheat leaf segments in the dark. The newly prepared substituted cytokinin derivatives of the general formula I showed stronger anti-senescent activity in dark conditions in comparison to the classical cytokinin kinetin (Kin).

TABLE 3

The effect of novel compounds on delaying of senescence in detached leaf segments of *Triticum aestivum* cv. Hereward in dark conditions

| No | Tested compound | concentration with highest activity (mol. $l^{-1}$) | activity (%) [$10^{-4}$ mol. $l^{-1}$ Kin = 100%] |
|---|---|---|---|
|  | 6-furfurylaminopurine | $10^{-4}$ | 100 |
| 1 | 6-furfurylamino-9-(2-chloroethyl)purine | $10^{-4}$ | 120 (±15) |
| 2 | 6-furfurylamino-9-(2-bromoethyl)purine | $10^{-4}$ | 102 (±3) |
| 38 | 3-methoxy-benzylamino-9-(2-chloroethyl)purine | $10^{-4}$ | 116 (±7) |
| 47 | 3-hydroxy-benzylamino-9-(2-chloroethyl)purine | $10^{-4}$ | 111 (±9) |
| 136 | 6-(E)-(4-hydroxy-1,3-dimethylbut-2-en-1-ylamino)-9-(2-chloroethyl)purine | $10^{-4}$ | 114 (±4) |
|  | 6-furfurylamino-9-(4-chlorobutyl)purine | $10^{-4}$ | 72 (±13) |
|  | 6-furfurylamino-9-(4-bromobutyl)purine | $10^{-4}$ | 1.2 (±2) |

Example 9

Figure 2:
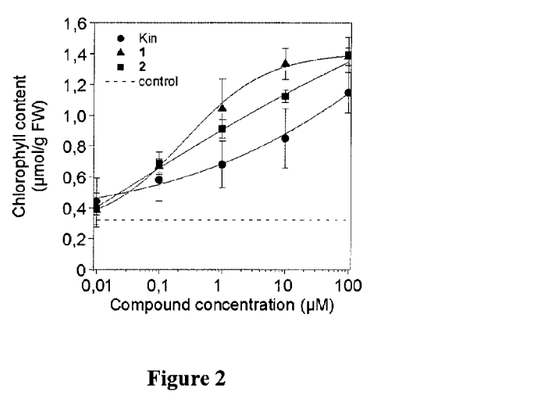
FIG. 2 displays the comparison of the effect of 1 and 2 and their parent classical cytokinin kinetin on retention of chlorophyll content in detached leaf segments of *Triticum aestivum* cv. Hereward during senescence in light conditions. Error bars show SD (n=3).

Anti-Senescent Activity of Novel Compounds Tested in Senescent Bioassay on Wheat Leaf Segments in the Light Conditions The ability of the novel compounds to retard chlorophyll degradation in detached wheat leaves was tested also in the light conditions. The experiment was performed as described in Example 7 with modifications as follows—the incubation of the leaves with the compounds was done in the constant light (100 µmol·m$^{-2}$·s$^{-1}$) at 22° C. As shown in FIG. 2, the novel compounds have shown stronger positive effects to delaying of senescence in wheat leaf segments in light conditions in comparison with N9-unsubstituted parent cytokinin Kin.

As shown in FIG. 2 the novel compounds exhibited strong positive effect on delaying of senescence in wheat leaf segments in the light conditions in comparison to the N9-unsubstituted parent compound Kin. The compounds 1 and 2 prevented the chlorophyll degradation with high efficiency reaching 32-times and 18-times lower $EC_{50}$ than classical cytokinin Kin, respectively. The newly prepared substituted cytokinin derivatives of the general formula I thus showed stronger anti-senescent activity in light conditions in comparison to the classical cytokinin kinetin (Kin).

TABLE 4

The effect of novel compounds on delaying of senescence in detached leaf segments of *Triticum aestivum* cv. Hereward in light conditions.

| No | Tested compound | concentration with highest activity (mol. $l^{-1}$) | activity (%) [$10^{-4}$ mol. $l^{-1}$ Kin = 100%] |
|---|---|---|---|
|  | 6-furfurylaminopurin | $10^{-4}$ | 100 |
| 1 | 6-furfurylamino-9-(2-chlorethyl)purin | $10^{-5}$ | 116 (±7) |
| 2 | 6-furfurylamino-9-(2-bromethyl)purin | $10^{-4}$ | 121 (±8) |
|  | 6-furfurylamino-9-(4-chlorobutyl)purine | $10^{-4}$ | 119 (±6) |
|  | 6-furfurylamino-9-(4-bromobutyl)purine | $10^{-4}$ | 60 (±16) |

Example 10

Protection of Membrane Lipid Peroxidation in Wheat

A typical symptom associated with senescence as a direct consequence of increased reactive oxygen species is lipid peroxidation. Therefore the levels of MDA, a decomposition product of lipid peroxidation, were measured in detached wheat leaves that were exposed to the prepared novel derivatives and kinetin for four days in the dark as described in Example 7. MDA levels were measured using a thiobarbituric acid (TBA) method. In detail, 100 mg of fresh plant material was homogenized by high speed shaking in a ball mill (MM301, Retsch, Germany) with 1 mL of 80% methanol. The crude extract was centrifuged at 10,000×g for 5 min, and 100 µL aliquot of supernatant was vortexed with 100 µL of 0.5% (w/v) TBA containing 0.1% (w/v) trichloroacetic acid, and the resulting solution was then incubated for 30 min at 95° C. The samples were quickly cooled on ice and recentrifuged for 5 min at 1000×g. The absorbance of supernatant was measured at 532 nm with background subtraction at 600 nm and the amount of MDA-TBA complex was calculated from the coefficient of absorbance 155 mM$^{-1}$ cm$^{-1}$.

Novel derivatives 1 and 2 significantly reduced peroxidation of membrane lipids compared to untreated control (Table 5—the values express content of MDA, the decomposition product of membrane lipids). The compounds 1 and 2 reduced the level of membrane lipid peroxidation during the dark senescence in the detached wheat leaves to 67% and 69%, respectively.

The newly prepared derivatives of the general formula I thus had protective function against the negative action the reactive oxygen species that are highly accumulated in tissues during leaf senescence.

TABLE 5

The effect of novel compounds on lipid membrane peroxidation during the senescence of detached leaves of *Triticum aestivum* cv. Hereward in dark conditions.

| No | Tested compound | MDA (nmol/g FW) |
|---|---|---|
|  | Untreated control | 18.9 (±2.2) |
| 1 | 6-furfurylamino-9-(2-chloroethyl)purine | 12.8 (±1.0) |
| 2 | 6-furfurylamino-9-(2-bromoethyl)purine | 13.2 (±1.5) |

Example 11

Testing of Novel Compounds in *Amaranthus* Bioassay

The standard *Amaranthus* bioassay with several modifications was used to study cytokinin activity of the novel compounds. The seeds of *Amaranthus caudatus* var. *atropurpurea* were surface-sterilised in 10% (w/v) N-chlorobenzene-sulfonamide for 10 min and washed 5 times with deionized water. They were placed in 14 cm Petri dishes containing paper tissues saturated with deionized water. After 72 h of cultivation at 25° C. in darkness, the roots of the seedlings were cut off. The explants, consisting of two cotyledons and hypocotyl, were placed in 5 cm Petri dishes onto two layers of filter paper soaked with 1 ml of the incubation medium containing 10 μmol of $Na_2HPO_4$—$KH_2PO_4$, pH 6.8, 5 μmol of tyrosine and the cytokinin to be tested. There were 20 explants per dish. The procedure was carried out under a green safe light in a darkroom. After 48 h of incubation at 25° C. in darkness, betacyanin was extracted by freezing the explants in 4 ml 3.33 μM acetic acid. The concentration of betacyanin was determined from the absorbances at 537 nm and 620 nm as follows: $\Delta A = A_{537\ nm} - A_{620\ nm}$. The values $\Delta A$ were plotted against the concentration tested, are means of five replicates and the entire test was repeated twice. In each experiment activities of the novel compounds were tested and compared with activity of their N9-unsubstituted parent cytokinin iP, which is known to be highly active cytokinin. The compounds to be tested were dissolved in dimethylsulfoxide (DMSO) and the solution brought up to $10^{-3}$ M with distilled water. This stock solution was further diluted with the respective media used for the biotest to a concentration ranging from $10^{-8}$ M to $10^{-4}$ M. The final concentration of DMSO did not exceed 0.2% and therefore did not affect the biological activity in the assay system used. The activity obtained for $10^{-5}$ M iP was postulated as 100%.

The compound functioning as cytokinin should exhibit stimulatory effect on betacyanin production in *Amaranthus*. The results in Table 6 show that the newly prepared substituted derivatives of the general formula I showed stronger cytokinin activity in the *Amaranthus* bioassay than classical cytokinin iP.

TABLE 6

The effect of novel compounds on formation of betacyanin in the Amaranthus hypocotyls in the dark

| No | Tested compound | concentration with highest activity (mol. $l^{-1}$) | activity (%) [$10^{-5}$ mol. $l^{-1}$ iP = 100%] |
|---|---|---|---|
|   | 6-(3-methylbut-2-en-1-yl)aminopurine (iP) | $10^{-5}$ | 100 |
| 3 | 6-((3-methylbut-2-en-1-yl)amino)-9-(2-bromoethyl)purine | $10^{-4}$ | 116 (±9) |
| 4 | 6-((3-methylbut-2-en-1-yl)amino)-9-(2-chloroethyl)purine | $10^{-4}$ | 128 (±11) |

Example 12

N9-Alkyl Substituent of the Cytokinin Prevents Inhibitory Effect of Classical Cytokinin on Root Growth of Maize Cytokinins are known to be negative regulators of root elongation and lateral root formation (Werner, T. et al., *Proc Natl Acad Sci USA* 98, 10487-92, 2001) and their exogenously applied concentrations exceeding 1 μM often cause complete inhibition of the root growth.

To investigate in vivo effect of the new derivatives on the root growth and development, maize seeds (*Zea mays* cv. CELLUX, Morseva, Czech Republic) were imbibed in tap water and germinated in dark on a wetted filter paper. After 2 days, the germinated seedlings were transferred to aerated hydroponic tanks filled with Hoagland's nutrient solution (fifteens per one liter of Hoagland solution). The plants were grown in a chamber with 16 hrs light (250 μm-2 s-1) at 27° C. and 8 hrs dark period at 20° C. The nutrient solution was supplemented with 5 μM and 10 μM concentration of 6-furfurylamino-9-(2-chloroethyl)purine or 5 μM cytokinin kinetin (Kin). All solutions used for cytokinin treatment including negative control contained DMSO in final concentration of 0.01%.

Figure 3:
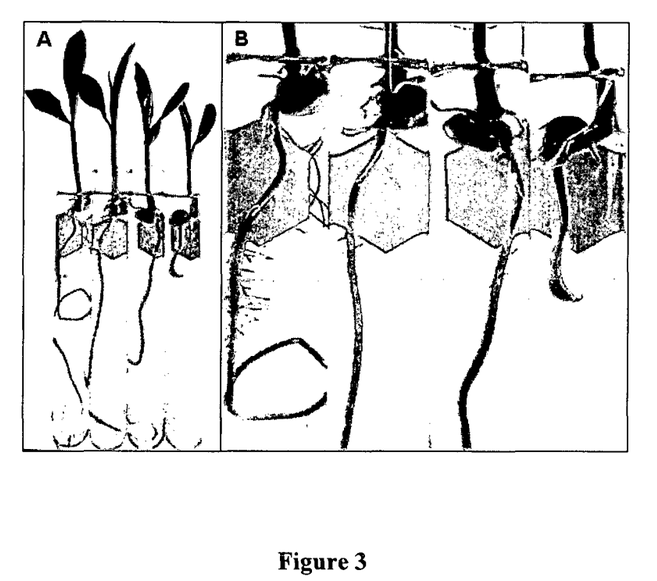
FIG. 3 shows the phenotype of kinetin $N^9$-substituted derivatives treated *Z. mays* seedlings. A and B left to right: DMSO control; 5 μM compound 1; 10 μM compound 1; 5 μM kinetin. Whole maize seedlings (A) with a detail of lateral roots (B).
Figure 4:
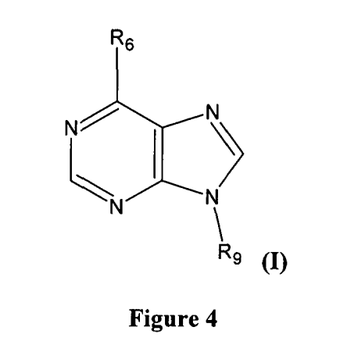
FIG. 4 represents formula (I)

FIG. 3 documents that after application of 5 μM of compound 1 root and shoot phenotypes of maize plants were almost identical to DMSO treated negative control (FIG. 3). When 10 μM compound 1 was applied only slightly reduced length of primary and lateral roots was detected, whilst already 5 μM concentration of kinetin caused dramatic thickening and shortening of primary root with no lateral root formation (FIG. 3).

VP14 encodes for 9-cis-epoxycarotenoid dioxygenase responsible for abscisic acid biosynthesis and its abundance suggests whether the plant is under stress condition (Schwarz et al., 2003, Plant Phys., 131, 1591-1601). Abscisic acid has a direct effect on up-regulation of genes involved in stress responses (Tan et al., 1997, Proc Natl Acad Sci USA, 94, 12235-40). 5-days-old maize seedlings were carefully transferred from substrate to nutrient solution supplemented with tested compound in 5 μM concentration and were cultivated for another 3 days. Transcript copy number of VP14 gene was determined in roots and leaves of treated plants independently by method of reverse transcription polymerase chain reaction. In Table 7 is shown that whereas commonly used cytokinin-kinetin significantly increases VP14 expression in both root and leaves of maize, compound 1 does not induce any stress response.

This indicates that the newly prepared substituted derivatives of the general formula I do not have negative effect on the root growth and development in the high concentrations in contrast to classical cytokinin kinetin and can be thus used with advantage for the root treatments in broader concentration range than classical cytokinins.

TABLE 7

The effect of new compounds on expression VP14 stress gene in intact maize plants (*Zea mays* L.).
(Relative values of transcript number, related to untreated control)

| | | Relative amount of transcripts | |
|---|---|---|---|
| No | Tested compound | root | leaf |
| | Untreated control | 1 | 1 |
| | 6-furfurylaminopurine | 3.4 (±0.8) | 16.3 (±4.0) |
| 1 | 6-furfurylamino-9-(2-chloroethyl)purine | 0.4 (±0.1) | 1.1 (±0.3) |

Example 13

Formulations

Active ingredient mixture comprising a compound or mixture of compounds of formula I.

| A1. Emulsifiable concentrates | a) | b) | c) | d) |
|---|---|---|---|---|
| active ingredient mixture | 5% | 10% | 25% | 50% |
| calcium dodecylbenzenesulfonate | 6% | 8% | 6% | 8% |
| castor oil polyglycol ether (36 mol of ethylene oxide) | 4% | — | 4% | 4% |
| octylphenol polyglycol ether (7-8 mol of ethylene oxide) | 2% | — | 2% | — |
| cyclohexanone | — | — | 10% | 20% |
| arom. hydrocarbon mixture $C_9$—$C_{12}$ | 83% | 82% | 53% | 18% |

Emulsions of any desired concentration can be obtained from such concentrates by dilution with water.

| A2. Solutions | a) | b) | c) | d) |
|---|---|---|---|---|
| active ingredient mixture | 5% | 10 % | 50% | 90% |
| 1-methoxy-3-(3-methoxy-propoxy)-propane | — | 20 % | 20% | — |
| polyethylene glycol MW 400 | 20% | 10 % | — | — |
| N-methyl-2-pyrrolidone | — | — | 30% | 10% |
| arom. hydrocarbon mixture $C_9$—$C_{12}$ | 75% | 60% | — | — |

The solutions are suitable for use in the form of microdrops.

| A3. Wettable powders | a) | b) | c) | d) |
|---|---|---|---|---|
| active ingredient mixture | 5% | 25% | 50% | 80% |
| sodium lignosulfonate | 4% | — | 3% | — |
| sodium lauryl sulfate | 2% | 3% | — | 4% |
| sodium diisobutylnaphthalene-sulfonate | — | 6% | 5% | 6% |
| octylphenol polyglycol ether (7-8 mol of ethylene oxide) | 1% | 2% | — | — |
| highly dispersed silicic acid | 1% | 3% | 5% | 10% |
| kaolin | 87% | 61% | 37% | — |

The active ingredient is mixed thoroughly with the adjuvants and the mixture is thoroughly ground in a suitable mill, affording wettable powders which can be diluted with water to give suspensions of any desired concentration.

| A4. Coated granules | a) | b) | c) |
|---|---|---|---|
| active ingredient mixture | 0.1% | 5% | 15% |
| highly dispersed silicic acid | 0.9% | 2% | 2% |
| inorganic carrier (.AE 0.1 –1 mm) e.g. $CaCO_3$ or $SiO_2$ | 99.0% | 93% | 83% |

The active ingredient is dissolved in methylene chloroide and applied to the carrier by spraying, and the solvent is then evaporated off in vacuo.

| A5. Coated granules | a) | b) | c) |
|---|---|---|---|
| active ingredient mixture | 0.1% | 5% | 15% |
| polyethylene glycol MW 200 | 1.0% | 2% | 3% |
| highly dispersed silicic acid | 0.9% | 1% | 2% |
| inorganic carrier (AE 0.1 –1 mm) e.g. $CaCO_3$ or $SiO_2$ | 98.0% | 92% | 80% |

The finely ground active ingredient is uniformly applied, in a mixer, to the carrier moistened with polyethylene glycol. Non-dusty coated granules are obtained in this manner.

| A6. Extruder granules | a) | b) | c) | d) |
|---|---|---|---|---|
| active ingredient mixture | 0.1% | 3% | 5% | 15% |
| sodium lignosulfonate | 1.5% | 2% | 3% | 4% |
| carboxymethylcellulose | 1.4% | 2% | 2% | 2% |
| kaolin | 97% | 93% | 90% | 79% |

The active ingredient is mixed and ground with the adjuvants, and the mixture is moistened with water. The mixture is extruded and then dried in a stream of air.

| A7. Dusts | a) | b) | c) |
|---|---|---|---|
| active ingredient mixture | 0.1% | 1% | 5% |
| talcum | 39.9% | 49% | 35% |
| kaolin | 60% | 50% | 60% |

Ready-to-use dusts are obtained by mixing the active ingredient with the carriers and grinding the mixture in a suitable mill.

| A8. Suspension concentrates | a) | b) | c) | d) |
|---|---|---|---|---|
| active ingredient mixture | 3% | 10% | 25% | 50% |
| ethylene glycol | 5% | 5% | 5% | 5% |
| nonylphenol polyglycol ether (15 mol of ethylene oxide) | 1% | 2% | — | — |
| sodium lignosulfonate | 3% | 3% | 4% | 5% |
| carboxymethylcellulose | 1% | 1% | 1% | 1% |
| 37% aqueous formaldehyde solution | 0.2% | 0.2% | 0.2% | 0.2% |
| silicone oil emulsion | 0.8% | 0.8% | 0.8% | 0.8% |
| water | 86% | 78% | 64% | 38% |

The finely ground active ingredient is intimately mixed with the adjutants, giving a suspension concentrate from which suspensions of any desired concentration can be obtained by dilution with water.

Example 14

Gel Formulation

The names of the formulation components are given according to the terminology of the registering authorities and their quantity is in grams per 100 g.

| Gel | /100 g |
|---|---|
| active compound 6-furfurylamino-9-(2-chloroethyl)purine | 1.0 g |
| butylhydroxytoluenum (Nipanox BHT) | 0.2 g |
| butylparaben (Nipabutyl) | 0.2 g |
| diethylene glycol monoethyl ether (Transcutol P) | 10.0 g |
| silica colloidalis anhydrica (Zeopharm 177) | 5.0 g |
| propylene glycol laurate (Lauroglycol FCC) | 83.6 g |

The gel consistence may be additionally modified by addition of silica colloidalis anhydrica. It is again expected that the transdermal Transcutol P/Lauroglycol FCC system will increase the efficiency of active compound. Silica colloidalis anhydrica will probably slow down the penetration of the active substance.

The invention claimed is:
1. A method of regulating the growth and development of at least one of plant cells, plant organs, and whole plants, the method comprising administering one or more compounds of formula I,

(I)

wherein:

$R_6$ is selected from the group comprising —NH-furfuryl, —NH-(4-hydroxy-3-methylbut-2-en-1-yl), —NH-(3-methylbut-2-en-1-yl), —NH-(4-hydroxy-3-methylbutyl), —NH-(4-hydroxy-1,3-dimethylbut-2-en-1-yl), —NH-(4-hydroxy-1,3-dimethylbutyl), —NH-benzyl, —NH-phenyl, wherein benzyl, furfuryl and phenyl can be unsubstituted or substituted with 1 to 3 substituents selected from the group comprising hydroxy, halogen, methyl and methoxy; and $R_9$ is selected from the group comprising $C_1$-$C_3$ alkyl and $C_2$-$C_3$ alkenyl wherein $C_1$-$C_3$ alkyl is substituted with one or more halogen atoms and wherein $C_2$-$C_3$ alkenyl is substituted on a terminal carbon atom with one or two halogen atoms;

provided that:
if $R_9$ is 2-chloroethyl, $R_6$ is not —NH-furfuryl, —NH-benzyl; and
if $R_9$ is 3-chloropropyl or 2-bromoethyl, $R_6$ cannot be —NH-benzyl.

2. The method of claim 1, wherein the compound of formula I is selected from the group consisting of:

6-(furfurylamino)-9-(chloromethyl, 3-chloropropyl, bromomethyl, 2-bromoethyl, 3-bromopropyl, 2,2-dichloroethyl, 2-chlorovinyl, 2-bromovinyl)purine, 6-(2-chlorobenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(3-chlorobenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(3-fluorobenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(3-hydroxybenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(3-methoxybenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(3-methylbut-2-en-1-ylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-benzylamino-9-(chloromethyl, bromomethyl, 3-bromopropyl, 2,2-dichloroethyl, 2-chlorovinyl, 2-bromovinyl)purine, 6-(4-hydroxy-3-methylbut-2-en-1-ylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(Z)-(4-hydroxy-3-methylbut-2-en-1-ylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(E)-(4-hydroxy-3-methylbut-2-en-1-ylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(Z)-(4-hydroxy-1,3-dimethylbut-2-en-1-ylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(E)-(4-hydroxy-1,3-dimethylbut-2-en-1-ylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(4-hydroxy-1,3-dimethylbutylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(4-hydroxy-3-methylbutylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-phenylamino-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(3-methoxyphenylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(2-methoxybenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(2-hydroxybenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine, 6-(2-fluorobenzylamino)-9-(chloromethyl, 2-chloroethyl, 3-chloropropyl, bromomethyl, 2-bromoethyl, 3-bromopropyl, 2,2-dichloroethyl, 2-chlorovinyl, 2-bromovinyl)purine.

3. The method of claim 1, wherein the regulation of growth and development of plant cells, organs and/or whole plants includes stimulation of plant organogenesis leading to enlargement of plant root system.

4. The method of claim 1, wherein the regulation of growth and development of plant cells, organs and/or whole plants includes at least one of: increase of grain size of monocotyledonous plants, increase of fruit size of monocotyledonous plants, and shortening of plant seed germination time.

5. The method of claim 1, wherein the regulation of growth and development of plant cells, organs and/or whole plants includes at least one of: regulation of proliferation, regulation of morphogenesis, inhibition of senescence, and inhibition of stress.

6. The method of claim 1, wherein the regulation of growth and development of plant cells, organs and/or whole plants includes at least one of: delaying of chlorophyll degradation, and delaying senescence of plant tissues.

7. The method of claim 1, wherein the regulation of growth and development of plant cells, organs and/or whole plants includes an increase of at least one of yield and quality of monocotyledonous plants.

8. The method of claim 1, wherein the at least one compound of formula I is administered, as part of a preparation, to plant cells in culture.

9. The method of claim 1, wherein the at least one compound of formula I is administered as part of a preparation.

10. Compounds of formula Ia wherein:
- $R_6$ is selected from the group containing —NH-furfuryl, —NH-(4-hydroxy-3-methylbut-2-en-1-yl), —NH-(3-methylbut-2-en-1-yl), —NH-(4-hydroxy-3-methylbutyl), —NH-(4-hydroxy-1,3-dimethylbut-2-en-1-yl), —NH-(4-hydroxy-1,3-dimethylbutyl), —NH-benzyl, —NH-phenyl, wherein benzyl, furfuryl and phenyl can be unsubstituted or optionally substituted with 1 to 3 substituents selected from the group comprising hydroxy, halogen, methyl and methoxy, and
- $R_9$ is selected from the group comprising $C_1$-$C_3$ alkyl wherein $C_1$-$C_3$ alkyl is substituted with one or more halogen atoms;

provided that:
if $R_9$ is 2-chloroethyl, $R_6$ cannot be —NH-furfuryl, —NH-benzyl;
if $R_9$ is 3-chloropropyl or 2-bromoethyl, $R_6$ cannot be —NH-benzyl; and
if $R_9$ is 2,2-dichloroethyl, $R_6$ cannot be —NH-(4-hydroxy-3-methylbutyl) or —NH-(3-methylbut-2-en-1-yl).

11. Compounds of formula Ia according to claim 10, wherein:
- $R_6$ is selected from the group containing —NH-furfuryl, —NH-(4-hydroxy-3-methylbut-2-en-1-yl), —NH-(3-methylbut-2-en-1-yl), —NH-(4-hydroxy-1,3-dimethylbut-2-en-1-yl), —NH-(4-hydroxy-1,3-dimethylbutyl), —NH-benzyl, —NH-phenyl, wherein benzyl, furfuryl and phenyl can be unsubstituted or optionally substituted with 1 to 3 substituents selected from the group comprising hydroxy, halogen, methyl and methoxy.

12. A preparation comprising at least one compound of formula Ia of claim 10, and one or more auxiliary substances; wherein the auxiliary substances are selected from the group consisting of diluents, carriers, fillers, preservatives, stabilizers, wetting agents, emulsifiers, solubilizing agents, fertilizers and micronutrient donors.

13. Compounds of formula Ia wherein
- $R_6$ is selected from the group containing —NH-furfuryl, —NH-(4-hydroxy-3-methylbut-2-en-1-yl), —NH-(3-methylbut-2-en-1-yl), —NH-(4-hydroxy-3-methylbutyl), —NH-(4-hydroxy-1,3-dimethylbut-2-en-1-yl), —NH-(4-hydroxy-1,3-dimethylbutyl), —NH-benzyl, —NH-phenyl, wherein benzyl, furfuryl and phenyl can be unsubstituted or optionally substituted with 1 to 3 substituents selected from the group comprising hydroxy, halogen, methyl and methoxy;
- $R_9$ is $C_1$-$C_3$ alkyl, wherein $C_1$-$C_3$ alkyl is substituted with one halogen atom;

provided that
if $R_9$ is 2-chloroethyl, $R_6$ cannot be —NH-furfuryl, —NH-benzyl; and
if $R_9$ is 3-chloropropyl or 2-bromoethyl, $R_6$ cannot be —NH-benzyl.

14. A preparation comprising at least one compound of formula Ia of claim 13, and one or more auxiliary substances; wherein the auxiliary substances are selected from the group consisting of diluents, carriers, fillers, preservatives, stabilizers, wetting agents, emulsifiers, solubilizing agents, fertilizers and micronutrient donors.

15. Compounds of formula Ia according to claim 13, wherein:
- $R_6$ is selected from the group containing —NH-furfuryl, —NH-(4-hydroxy-3-methylbut-2-en-1-yl), —NH-(3-methylbut-2-en-1-yl), —NH-(4-hydroxy-1,3-dimethylbut-2-en-1-yl), —NH-(4-hydroxy-1,3-dimethylbutyl), —NH-benzyl, —NH-phenyl, wherein benzyl, furfuryl and phenyl can be unsubstituted or optionally substituted with 1 to 3 substituents selected from the group comprising hydroxy, halogen, methyl and methoxy.

16. The method of claim 1, wherein $R_9$ is $C_2$-$C_3$ alkenyl.

17. The method of claim 1, wherein $R_9$ is $C_2$ alkyl.

18. The method of claim 1, wherein $R_9$ is $C_1$ alkyl.

19. The method of claim 1, wherein $R_9$ is selected from $C_1$-$C_2$ alkyl and $C_2$-$C_3$ alkenyl.

* * * * *